(12) United States Patent
Kiselev

(10) Patent No.: US 10,040,837 B2
(45) Date of Patent: Aug. 7, 2018

(54) NUCLEOTIDE SEQUENCE AND PHARMACEUTICAL COMPOSITION BASED THEREON WITH PROLONGED VEGF TRANSGENE EXPRESSION

(71) Applicant: "NEXTGEN" COMPANY LIMITED, Moscow (RU)

(72) Inventor: Sergej L'vovich Kiselev, Moscow (RU)

(73) Assignee: "NEXTGEN" COMPANY LIMITED, Moscow (RU)

( * ) Notice: Subject to any disclaimer, the term of this patent is extended or adjusted under 35 U.S.C. 154(b) by 0 days.

(21) Appl. No.: 15/819,157

(22) Filed: Nov. 21, 2017

(65) Prior Publication Data
US 2018/0086800 A1 Mar. 29, 2018

Related U.S. Application Data

(62) Division of application No. 15/070,239, filed on Mar. 15, 2016, now Pat. No. 9,896,493.

(30) Foreign Application Priority Data

May 26, 2015 (RU) ................................ 2015119768

(51) Int. Cl.
*C07K 14/475* (2006.01)
*A61K 31/00* (2006.01)
*C12N 15/67* (2006.01)

(52) U.S. Cl.
CPC ............ *C07K 14/475* (2013.01); *A61K 31/00* (2013.01); *C12N 15/67* (2013.01); *C12N 2830/50* (2013.01)

(58) Field of Classification Search
CPC ....... A61K 31/00; C12N 15/67; C07K 14/475
See application file for complete search history.

(56) References Cited

U.S. PATENT DOCUMENTS

| | | | |
|---|---|---|---|
| 5,587,300 | A | 12/1996 | Malter |
| 6,153,407 | A | 11/2000 | Sytkowski et al. |
| 6,613,563 | B1 | 9/2003 | Sosnowski |
| 6,627,436 | B2 | 9/2003 | Sorge et al. |
| 7,709,450 | B2 | 5/2010 | Eriksson et al. |
| 2003/0203844 | A1 | 10/2003 | Delfani |
| 2008/0081366 | A1 | 4/2008 | Musunuri et al. |
| 2011/0117107 | A1 | 5/2011 | Stiles |
| 2011/0178158 | A1 | 7/2011 | Benet Ferrus et al. |
| 2012/0053333 | A1 | 3/2012 | Mauro et al. |
| 2015/0335711 | A1 | 11/2015 | Kiselev et al. |

FOREIGN PATENT DOCUMENTS

| | | |
|---|---|---|
| CN | 1351055 | 5/2002 |
| CN | 1389269 | 1/2003 |
| RU | 2 297 848 | 4/2007 |
| RU | 2 376 373 | 12/2009 |
| RU | 2 431 669 | 10/2011 |
| WO | WO 2000/047235 | 8/2000 |
| WO | WO 2004/050126 | 6/2004 |
| WO | 2006 029908 | 3/2006 |
| WO | 2006 074182 | 7/2006 |

OTHER PUBLICATIONS

Supplementary Partial Search Report dated Jul. 27, 2015, in European patent application No. 13832746.
Supplementary Search Report dated Nov. 17, 2015, in European patent application No. 13832746.
Search Report dated Jun. 15, 2015, in Canadian patent application No. 2,881,799.
Anghel et al, "Clinical improvement after treatment with VEGF165 in patients with severe chronic lower limb ischaemia", 2007, Genomic Med., vol. 1, No. 1-2, pp. 47-55.
Written Opinion of the International Searching Authority dated Jan. 23, 2014 in PCT/RU13/000669 Filed Aug. 2, 2013.
International Search Report dated Jan. 23, 2014 in PCT/RU13/000669 Filed Aug. 2, 2013.
Office Action dated Jan. 7, 2016, in Canadian Patent Application No. 2,881,799.
Schender, V.O., et al., "Simulating the *E.coli* Producer pCMV-VEGF165 Recombinant Strain Fermentation for Therapeutic Plasmid DNA Production", The Russian Chemical and Technology University Named After Mendeleev D.I., pp. 30-31, (May 24, 2011) (with English translation).
"Neovasculgen", Registration Certificate for Pharmaceutical Composition for Medical Application, LP0-00671, URL:http://hsci.ru/o-kompanii/litsenzii, Total 1 Page, (Sep. 28, 2011).
"Instruction for medical application of Neovasculgen®". URL:http://medi.ru/doc/a4101.htm. pp. 1-4. (Mar. 2012).
"Neovasculgen®", URL: http://medi.ru/doc/a410100.htm, pp. 1-2, (Apr. 2012) Printed on Jul. 10, 2013.
"Safety and Efficacy Study Using Gene Therapy for Critical Lumb Ischemia", clinicaltrials.gov, pp. 1-4, (Mar. 5, 2012).
"Efficacy and Safety Study of NV1FGF in Patients With Severe Peripheral Artery Occlusive Disease. (TALISMAN202)", clinicaltrials.gov, pp. 1-3, (Nov. 24, 2008).
Shvalb, P.G., et al., "Efficacy and safety of application «Neovasculgen» in the complex treatment patients with chronic lower limb ischemia(IIb-III phase of clinical trials)", Clinical Experiment, vol. I, No. 3, Total 8 Pages, (2011) (with English abstract).
Kusumanto, Y.H., et al., "Treatment with intramuscular vascular endothelial growth factor gene compared with placebo for patients with diabetes mellitus and critical limb ischemia: a double-blind randomized trial.", Hum Gene Ther., URL:http://www.ncbi.nlm.nih.gov/pubmed/16776576, vol. 17, No. 6, Total 1 Page, (Jun. 2006) (English translation only).
Arutyunian et al, "Role of VEGF-A165 receptors in angiogenesis" Cellular Transplantology and Tissue, 2013; VIII(1): 12-18 (with English abstract).

(Continued)

*Primary Examiner* — Antonio Galisteo Gonzalez
(74) *Attorney, Agent, or Firm* — Oblon, McClelland, Maier & Neustadt, L.L.P.

(57) ABSTRACT

A nucleic acid or transgene comprising a modified VEGF 3'-untranslated region (3'-UTR) polynucleotide sequence and a polynucleotide sequence encoding a Vascular Endothelial Growth Factor (VEGF). When transformed into a host cell, the nucleic acid or transgene exhibits a high stability and provides prolonged and reliable expression of VEGF. A method for extending the lifetime of transgene mRNA encoding VEGF in a mammalian host cell. A method for treating a subject in need of increased or modified expression of VEGF using this nucleic acid or transgene.

9 Claims, 5 Drawing Sheets
(5 of 5 Drawing Sheet(s) Filed in Color)

(56) References Cited

OTHER PUBLICATIONS

Bhattacharya et al, "Distinct role of PLCβ3 in VEGF-mediated directional migration and vascular sprouting", J. Cell Sci. 2009; 122(Pt 7): 1025-34.

Berendsen et al, "How vascular endothelial growth factor-A (VEGF) regulates differentiation of mesenchymal stem cells", J. Histochem. Cytochem. 2014; 62(2): 103-8.

Baboo et al. "Dark matter" worlds of unstable RNA and protein, Nucleus 2014; 5(4): 281-6.

Coultas et al. "Endothelial cells and VEGF in vascular development", Nature 2005; 438(7070): 937-45.

D' Alimonte et al, "Vascular endothelial growth factor enhances in vitro proliferation and osteogenic differentiation of human dental pulp stem cells". J. Biol. Regul. Homeost. Agents. 2011; 25(1): 57-69.

Folkman et al, "Isolation of a tumor factor responsible for angiogenesis", J. Exp. Med. 1971; 133(2): 275-88.

Geiger et al. "Vascular endothelial growth factor gene-activated matrix (VEGF165-GAM) enhances osteogenesis and angiogenesis in large segmental bone defects", J. Bone Miner. Res. 2005; 20(11): 2028-35.

Grigorian et al, "Some possible molecular mechanisms of VEGF coding plasmids functioning", Cell. Transpl. Tiss. Engin. 2011. VI (3): 24-8 (with English abstract).

Goel et al. "VEGF targets the tumour cell", Nat. Rev. Cancer, 2013; 13(12): 871-82.

Hillenbrand et al, "Vascular endothelial growth factor gene therapy improves nerve regeneration in a model of obstetric brachial plexus palsy", Neurol. Res. 2015; 37(3): 197-203.

Koch et al, "Signal transduction by vascular endothelial growth factor receptors", Cold Spring Harb. Perspect. Med. 2012; 2(7): a006502.

Ma et al, "Research progress in cytokines and signaling pathways for promoting pulmonary angiogenesis and vascular development", Zhongguo Dang Dai Er Ke Za Zhi. 2013; 15(9): 800-5 (with English abstract).

Marini et al, "Expression and localization of VEGF receptors in human fetal skeletal tissues", Histol. Histopathol. 2012; 27(12): 1579-87.

Mayr-Wohlfart et al, "Vascular endothelial growth factor stimulates chemotactic migration of primary human osteoblasts", Bone 2002; 30(3): 472-7.

Matsumoto et al, "VEGF receptor-2 Y951 signaling and a role for the adapter molecule TSAd in tumor angiogenesis", EMBO J. 2005; 24(13): 2342-53.

Neve et al, "In vitro and in vivo angiogenic activity of osteoarthritic and osteoporotic osteoblasts is modulated by VEGF and vitamin D3 treatment", Regul. Pept. 2013; 184: 81-4.

Olsson et al, "VEGF receptor signalling—in control of vascular function", Nat. Rev. Mol. Cell Biol. 2006; 7(5): 359-71.

Ropper et al, "Vascular Endothelial Growth Factor Gene Transfer for Diabetic Polyneuropathy: A Randomized, Double-Blinded Trial", Ann. Neurol. 2009; 65(4): 386-93.

Tombran-Tink et al, "Osteoblasts and osteoclasts express PEDF, VEGF-A isoforms, and VEGF receptors: possible mediators of angiogenesis and matrix remodeling in the bone", Biochem. Biophys. Res. Commun. 2004; 316(2): 573-9.

Vislovukh et al. "Role of 3'-untranslated region translational control in cancer development, diagnostics and treatment", World J. Biol. Chem. 2014; 5(1): 40-57.

Williard, "Limb-saving medicines sought to prevent amputation", Nature Medicine 2012; 18(3): 328.

Yang et al, "The role of vascular endothelial growth factor in ossification", Int. J. Oral Sci. 2012; 4(2): 64-8.

Zavalishin et al, "Gene therapy of amyotrophic lateral sclerosis", Bull Exp Biol Med. 2008; 145(4): 483-6.

Zhao et al, "Effect of vascular endothelial growth factor 165 gene transfection on repair of bone defects and its mRNA expression in rabbits", Chinese Medical Journal 2007; 120(13); 1187-91.

Gene therapy clinical trials worldwide. http://www.abedia.com/wiley/years.php (accessed Mar. 18, 2016) 1 p.

Kessler, "Vascular endothelial growth factor gene transfer for diabetic polyneuropathy", Ann Neurol. 2009; 65(4): 362-4.

Cherviakov et al, "The opportunities for genic therapy of chronic obliterating diseases of lower limbs arteries", Hirurgiya 2014; (4): 40-5 (with partial English translation).

Zhao et al, "Effect of vascular endothelial growth factor 165 gene transfection on repair of bone defect: experiment with rabbits", Zhonghua Yi Xue Za Zhi. 2007; 87(25): 1778-82 (English abstract only 2 pp.).

A B C

SEQUENCE LISTING

```
<160> NUMBER OF SEQ ID NOS: 15

<210> SEQ ID NO 1
<211> LENGTH: 4859
<212> TYPE: DNA
<213> ORGANISM: Homo sapiens
<220> FEATURE:
<221> NAME/KEY: misc_feature
<222> LOCATION: (1)..(4859)
<223> OTHER INFORMATION: A nucleotide sequence of the original gene
      construction used for further modifications. Starting point -
      first nucleotide.

<400> SEQUENCE: 1
tatgccaagt acgcccccta ttgacgtcaa tgacggtaaa tggcccgcct ggcattatgc      60
ccagtacatg accttatggg actttcctac ttggcagtac atctacgtat tagtcatcgc     120
tattaccatg gtgatgcggt tttggcagta catcaatggg cgtggatagc ggtttgactc     180
acggggattt ccaagtctcc acccattga cgtcaatggg agtttgtttt ggcaccaaaa      240
tcaacgggac tttccaaaat gtcgtaacaa ctccgcccca ttgacgcaaa tgggcggtag     300
gcgtgtacgg tgggaggtct atataagcag agctggttta gtgaaccgtc agatccgcta     360
gtggatccaa agaattcggg cctccgaaac catgaacttt ctgctgtctt gggtgcattg     420
gagccttgcc ttgctgctct acctccacca tgccaagtgg tcccaggctg cacccatggc     480
agaaggagga gggcagaatc atcacgaagt ggtgaagttc atggatgtct atcagcgcag     540
ctactgccat ccaatcgaga ccctggtgga catcttccag gagtaccctg atgagatcga     600
gtacatcttc aagccatcct gtgtgcccct gatgcgatgc gggggctgct gcaatgacga     660
gggcctggag tgtgtgccca ctgaggagtc caacatcacc atgcagatta tgcggatcaa     720
acctcaccaa ggccagcaca taggagagat gagcttccta cagcacaaca atgtgaatg     780 cagaccaaag aaagatagag caagacaaga aaatccctgt gggccttgct cagagcggag     840
aaagcatttg tttgtacaag atccgcagac gtgtaaatgt tcctgcaaaa acacagactc     900
gcgttgcaag gcgaggcagc ttgagttaaa cgaacgtact tgcagatgtg acaagccgag     960
gcggtgaccc gggtggggta ccaggtaagt gtacccaatt cgccctatag tgagtcgtat    1020
tacaattcac tggccgtcgt tttacaacgt cgtgactggg aaaaccctgg cgttacccca    1080
acttaatcgc cttgcagcac atccccctt tcgccagctg gcgtaatagc gaagaggccc     1140
gcaacgaatc gcccttccc aacagttgcg caagcctgaa tggccgaatg gagatccaat    1200
ttttaagtgt ntaatgtgtt aaactactga ttctaattgt ttgtgtatnt tagattcaca    1260
gtcccaaggc tcatttcagg cccctcagtc ctcacagtct gttcatgatc ataatcagcc    1320
ataccacatt tgtagaggtt ttacttgctt taaaaaacct cccacacctc ccctgaacc     1380
```

```
tgaaacataa aatgaatgca attgttgttg ttaacttgtt tattgcagct tataatggtt    1440
acaaataaag caatagcatc acaaatttca caaataaagc attttttca ctgcattcta     1500 gttgtggttt gtccaaactc atcaatgtat cttaaggcgt aaattgtaag cgttaatatt    1560
ttgttaaaat tcgcgttaaa tttttgttaa atcagctcat tttttaacca ataggccgaa    1620
atcggcaaaa tcccttataa atcaaaagaa tagaccgaga tagggttgag tgttgttcca    1680
gtttggaaca agagtccact attaaagaac gtggactcca acgtcaaagg gcgaaaaacc    1740
gtctatcagg gcgatggccc actacgtgaa ccatcaccct aatcaagttt ttggggtcg     1800 aggtgccgta aagcactaaa tcggaaccct aaagggagcc cccgatttag agcttgacgg    1860
ggaaagccgg cgaacgtggc gagaaaggaa gggaagaaag cgaaaggagc gggcgctagg    1920
gcgctggcaa gtgtagcggt cacgctgcgc gtaaccacca cacccgccgc gcttaatgcg    1980
ccgctacagg gcgcgtcagg tggcactttt cggggaaatg tgcgcggaac ccctatttgt    2040 ttattttct aaatacattc aaatatgtat ccgctcatga acaataaccc tgataaatg      2100 cttcaataat attgaaaaag gaagagtcct gaggcggaaa gaaccagctg tggaatgtgt    2160
gtcagttagg gtgtggaaag tccccaggct ccccagcagg cagaagtatg caaagcatgc    2220
atctcaatta gtcagcaacc aggtgtggaa agtccccagg ctccccagca ggcagaagta    2280
tgcaaagcat gcatctcaat tagtcagcaa ccatagtccc gcccctaact ccgcccatcc    2340
cgcccctaac tccgcccagt tccgcccatt ctccgcccca tggctgacta atttttttta   2400
tttatgcaga ggccgaggcc gcctcggcct ctgagctatt ccagaagtag tgaggaggct    2460 ttttggagg cctaggcttt tgcaaagatc gatcaagaga caggatgagg atcgtttcgc     2520
atgattgaac aagatggatt gcacgcaggt tctccggccg cttgggtgga gaggctattc    2580
ggctatgact gggcacaaca gacaatcggc tgctctgatg ccgccgtgtt ccggctgtca    2640 gcgcagggc gcccggttct ttttgtcaag accgacctgt ccggtgccct gaatgaactg     2700
caagacgagg cagcgcggct atcgtggctg gccacgacgg gcgttccttg cgcagctgtg    2760
ctcgacgttg tcactgaagc gggaagggac tggctgctat tgggcgaagt gccggggcag    2820
gatctcctgt catctcacct tgctcctgcc gagaaagtat ccatcatggc tgatgcaatg    2880
cggcggctgc atacgcttga tccggctacc tgcccattcg accaccaagc gaaacatcgc    2940
atcgagcgag cacgtactcg gatggaagcc ggtcttgtcg atcaggatga tctggacgaa    3000
gagcatcagg ggctcgcgcc agccgaactg ttcgccaggc tcaaggcgag catgcccgac    3060
ggcgaggatc tcgtcgtgac ccatggcgat gcctgcttgc cgaatatcat ggtggaaaat    3120
ggccgctttt ctggattcat cgactgtggc cggctgggtg tggcggaccg ctatcaggac    3180
atagcgttgg ctacccgtga tattgctgaa gagcttggcg gcgaatgggc tgaccgcttc    3240
ctcgtgcttt acggtatcgc cgctcccgat tcgcagcgca tcgccttcta tcgccttctt    3300
gacgagttct tctgagcggg actctggggt tcgaaatgac cgaccaagcg acgcccaacc    3360
tgccatcacg agatttcgat tccaccgccg ccttctatga aggttgggc ttcggaatcg     3420 ttttccggga cgccggctgg atgatcctcc agcgcgggga tctcatgctg gagttcttcg    3480 cccacccta ggggaggcta actgaaacac ggaaggagac aataccgaa ggaacccgcg      3540 ctatgacggc aataaaaaga cagaataaaa cgcacggtgt tgggtcgttt gttcataaac    3600
gcggggttcg gtcccaggc tggcactctg tcgatacccc accgagaccc cattgggcc      3660 aatacgcccg cgtttcttcc ttttccccac cccacccccc aagttcgggt gaaggcccag    3720
```

```
ggctcgcagc caacgtcggg gcggcaggcc ctgccatagc ctcaggttac tcatatatac    3780
tttagattga tttaaaactt cattttaatt ttaaaaggat ctaggtgaag atcctttttg    3840
ataatctcat gaccaaaatc ccttaacgtg agttttcgtt ccactgagcg tcagaccccg    3900
tagaaaagat caaaggatct tcttgagatc cttttttttct gcgcgtaatc tgctgcttgc    3960
aaacaaaaaa accaccgcta ccagcggtgg tttgtttgcc ggatcaagag ctaccaactc    4020 ttttttccgaa ggtaactggc ttcagcagag cgcagatacc aaatactgtt cttctagtgt    4080
agccgtagtt aggccaccac ttcaagaact ctgtagcacc gcctacatac ctcgctctgc    4140
taatcctgtt accagtggct gctgccagtg gcgataagtc gtgtcttacc gggttggact    4200
caagacgata gttaccggat aaggcgcagc ggtcgggctg aacggggggt tcgtgcacac    4260
agcccagctt ggagcgaacg acctacaccg aactgagata cctacagcgt gagctatgag    4320
aaagcgccac gcttcccgaa gggagaaagg cggacaggta tccggtaagc ggcagggtcg    4380
gaacaggaga gcgcacgagg gagcttccag ggggaaacgc ctggtatctt tatagtcctg    4440
tcgggtttcg ccacctctga cttgagcgtc gatttttgtg atgctcgtca ggggggcgga    4500
gcctatggaa aaacgccagc aacgcggcct ttttacggtt cctggccttt tgctggcctt    4560
ttgctcacat gttctttcct gcgttatccc ctgattctgt ggataaccgt attaccgcca    4620
tgcattagtt attaatagta atcaattacg gggtcattag ttcatagccc atatatggag    4680
ttccgcgtta cataacttac ggtaaatggc ccgcctggct gaccgcccaa cgacccccgc    4740
ccattgacgt caataatgac gtatgttccc atagtaacgc caatagggac tttccattga    4800
cgtcaatggg tggagtattt acggtaaact gcccacttgg cagtacatca agtgtatca    4859
```

<210> SEQ ID NO 2
<211> LENGTH: 527
<212> TYPE: DNA
<213> ORGANISM: Homo sapiens
<220> FEATURE:
<221> NAME/KEY: misc_feature
<222> LOCATION: (1)..(527)
<223> OTHER INFORMATION: A fragment from 1070 bp to 1600 bp of SEQ ID
NO: 1 with deletion c1071, substitution a for c 1144, deletion
a1148.

<400> SEQUENCE: 2

```
ggttacccaa cttaatcgcc ttgcagcaca tcccccttttt cgccagctgg cgtaatagcg     60
aagaggcccg cacgatcgcc ccttcccaac agttgcgcaa gcctgaatgg ccgaatggag    120
atccaatttt taagtgtnta atgtgttaaa ctactgattc taattgtttg tgtatnttag    180
attcacagtc ccaaggctca tttcaggccc ctcagtcctc acagtctgtt catgatcata    240
atcagccata ccacatttgt agaggtttta cttgctttaa aaaacctccc acacctcccc    300
ctgaacctga acataaaat gaatgcaatt gttgttgtta acttgtttat tgcagcttat    360
aatggttaca aataaagcaa tagcatcaca aatttcacaa ataaagcatt tttttcactg    420
cattctagtt gtggtttgtc caaactcatc aatgtatctt aaggcgtaaa ttgtaagcgt    480
taatattttg ttaaaattcg cgttaaattt tgttaaatc agctcat                   527
```

<210> SEQ ID NO 3
<211> LENGTH: 527
<212> TYPE: DNA
<213> ORGANISM: Homo sapiens
<220> FEATURE:
<221> NAME/KEY: misc_feature
<222> LOCATION: (1)..(527)
<223> OTHER INFORMATION: Fragment from 1070 bp to 1600 bp of SEQ ID NO: 1 with deletion c1071, deletion c 1079, deletion t 1111, substitution a for c 1144, deletion a 1148

<400> SEQUENCE: 3

| | | |
|---|---|---|
| ggttacccaa cttaatcgcc ttgcagcaca tcccccttc gccagctggc gtaatagcga | 60 |
| agaggcccgc accgatcgcc ccttcccaac agttgcgcaa gcctgaatgg ccgaatggag | 120 |
| atccaatttt taagtgtnta atgtgttaaa ctactgattc taattgtttg tgtatnttag | 180 |
| attcacagtc ccaaggctca tttcaggccc ctcagtcctc acagtctgtt catgatcata | 240 |
| atcagccata ccacatttgt agaggtttta cttgctttaa aaaacctccc acacctcccc | 300 |
| ctgaacctga aacataaaat gaatgcaatt gttgttgtta acttgtttat tgcagcttat | 360 |
| aatggttaca aataaagcaa tagcatcaca aatttcacaa ataaagcatt tttttcactg | 420 |
| cattctagtt gtggtttgtc caaactcatc aatgtatctt aaggcgtaaa ttgtaagcgt | 480 |
| taatattttg ttaaaattcg cgttaaattt ttgttaaatc agctcat | 527 |

<210> SEQ ID NO 4
<211> LENGTH: 527
<212> TYPE: DNA
<213> ORGANISM: Homo sapiens
<220> FEATURE:
<221> NAME/KEY: misc_feature
<222> LOCATION: (1)..(527)
<223> OTHER INFORMATION: A fragment from 1070 bp to 1600 bp of SEQ ID
    NO: 1 with deletion c1071, deletion t 1111, deletion a 1148,
    deletion c 1155

<400> SEQUENCE: 4

| | | |
|---|---|---|
| ggttaccccca acttaatcgc cttgcagcac atccccctt cgccagctgg cgtaatagcg | 60 |
| aagaggcccg caacgatcgc ccttcccaac agttgcgcaa gcctgaatgg ccgaatggag | 120 |
| atccaatttt taagtgtnta atgtgttaaa ctactgattc taattgtttg tgtatnttag | 180 |
| attcacagtc ccaaggctca tttcaggccc ctcagtcctc acagtctgtt catgatcata | 240 |
| atcagccata ccacatttgt agaggtttta cttgctttaa aaaacctccc acacctcccc | 300 |
| ctgaacctga aacataaaat gaatgcaatt gttgttgtta acttgtttat tgcagcttat | 360 |
| aatggttaca aataaagcaa tagcatcaca aatttcacaa ataaagcatt tttttcactg | 420 |
| cattctagtt gtggtttgtc caaactcatc aatgtatctt aaggcgtaaa ttgtaagcgt | 480 |
| taatattttg ttaaaattcg cgttaaattt ttgttaaatc agctcat | 527 |

<210> SEQ ID NO 5
<211> LENGTH: 526
<212> TYPE: DNA
<213> ORGANISM: Homo sapiens
<220> FEATURE:
<221> NAME/KEY: misc_feature
<223> OTHER INFORMATION: A fragment from 1070 bp to 1600 bp of SEQ ID
    NO: 1 with deletion c1071, deletion c 1079, deletion a 1148,
    deletion c 1155, deletion a 1173
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t

<400> SEQUENCE: 5

| | | |
|---|---|---|
| ggttacccaa cttaatcgcc ttgcagcaca tcccccttt cgccagctgg cgtaatagcg | 60 |
| aagaggcccg caacgatcgc ccttcccaac agttgcgcag cctgaatggc cgaatggaga | 120 |

```
tccaattttt aagtgtntaa tgtgttaaac tactgattct aattgtttgt gtatnttaga        180
ttcacagtcc caaggctcat ttcaggcccc tcagtcctca cagtctgttc atgatcataa        240
tcagccatac cacatttgta gaggttttac ttgctttaaa aaacctccca cacctccccc        300
tgaacctgaa acataaaatg aatgcaattg ttgttgttaa cttgtttatt gcagcttata        360
atggttacaa ataaagcaat agcatcacaa atttcacaaa taaagcattt ttttcactgc        420
attctagttg tggtttgtcc aaactcatca atgtatctta aggcgtaaat tgtaagcgtt        480 aatatttgt taaaattcgc gttaaatttt tgttaaatca gctcat                       526
```

<210> SEQ ID NO 6
<211> LENGTH: 527
<212> TYPE: DNA
<213> ORGANISM: Homo sapiens
<220> FEATURE:
<221> NAME/KEY: misc_feature
<222> LOCATION: (1)..(527)
<223> OTHER INFORMATION: A fragment from 1070 bp to 1600 bp of SEQ ID
      NO: 1 with deletion c 1079, substitution a for c 1144, deletion c
      1155, deletion a 1173, deletion g 1183

<400> SEQUENCE: 6

```
gcgttaccca acttaatcgc cttgcagcac atcccccttt tcgccagctg gcgtaatagc         60
gaagaggccc gcaccgaatc gcccttccca acagttgcgc agcctgaatg ccgaatggag        120
atccaatttt taagtgtnta atgtgttaaa ctactgattc taattgtttg tgtatnttag        180
attcacagtc ccaaggctca tttcaggccc ctcagtcctc acagtctgtt catgatcata        240
atcagccata ccacatttgt agaggtttta cttgctttaa aaaacctccc acacctcccc        300
ctgaacctga acataaaaat gaatgcaatt gttgttgtta acttgtttat tgcagcttat        360
aatggttaca aataaagcaa tagcatcaca aatttcacaa ataaagcatt ttttcactg        420 cattctagtt gtggtttgtc caaactcatc aatgtatctt aaggcgtaaa ttgtaagcgt        480
taatattttg ttaaaattcg cgttaaattt tgttaaatc agctcat                      527
```

<210> SEQ ID NO 7
<211> LENGTH: 527
<212> TYPE: DNA
<213> ORGANISM: Homo sapiens
<220> FEATURE:
<221> NAME/KEY: misc_feature
<222> LOCATION: (1)..(527)
<223> OTHER INFORMATION: A fragment from 1070 bp to 1600 bp of SEQ ID
      NO: 1 with deletion t 1111, deletion a 1148, deletion g 1183,
      deletion c 1185, substitution g for c 1536

<400> SEQUENCE: 7

```
gcgttacccc aacttaatcg ccttgcagca catccccctt tcgccagctg gcgtaatagc         60
gaagaggccc gcaacgatcg ccccttccca acagttgcgc aagcctgaat gcgaatggag        120
atccaatttt taagtgtnta atgtgttaaa ctactgattc taattgtttg tgtatnttag        180
attcacagtc ccaaggctca tttcaggccc ctcagtcctc acagtctgtt catgatcata        240
atcagccata ccacatttgt agaggtttta cttgctttaa aaaacctccc acacctcccc        300
ctgaacctga acataaaaat gaatgcaatt gttgttgtta acttgtttat tgcagcttat        360
aatggttaca aataaagcaa tagcatcaca aatttcacaa ataaagcatt ttttcactg        420 cattctagtt gtggtttgtc caaactcatc aatgtatctt aacgcgtaaa ttgtaagcgt        480
taatattttg ttaaaattcg cgttaaattt tgttaaatc agctcat                      527
```

<210> SEQ ID NO 8
<211> LENGTH: 527
<212> TYPE: DNA
<213> ORGANISM: Homo sapiens
<220> FEATURE:
<221> NAME/KEY: misc_feature
<222> LOCATION: (1)..(527)
<220> FEATURE:
<221> NAME/KEY: misc_feature
<222> LOCATION: (1)..(527)
<223> OTHER INFORMATION: A fragment from 1070 bp to 1600 bp of SEQ ID
      NO: 1 with deletion t 1111, deletion a 1173, deletion g 1183,
      deletion c 1185, substitution g for c 1536

<400> SEQUENCE: 8
gcgttacccc aacttaatcg ccttgcagca catcccctt tcgccagctg gcgtaatagc      60
gaagaggccc gcaacgaatc gccccttccc aacagttgcg cagcctgaat gcgaatggag    120 atccaattt taagtgtnta atgtgttaaa ctactgattc taattgtttg tgtatnttag     180
attcacagtc ccaaggctca tttcaggccc ctcagtcctc acagtctgtt catgatcata    240
atcagccata ccacatttgt agaggtttta cttgctttaa aaacctccc acacctcccc    300 ctgaacctga aacataaaat gaatgcaatt gttgttgtta acttgtttat tgcagcttat    360
aatggttaca aataaagcaa tagcatcaca aatttcacaa ataaagcatt tttttcactg    420
cattctagtt gtggtttgtc caaactcatc aatgtatctt aacgcgtaaa ttgtaagcgt    480
taatattttg ttaaaattcg cgttaaattt ttgttaaatc agctcat                 527

<210> SEQ ID NO 9
<211> LENGTH: 526
<212> TYPE: DNA
<213> ORGANISM: Homo sapiens
<220> FEATURE:
<221> NAME/KEY: misc_feature
<222> LOCATION: (1)..(527)
<223> OTHER INFORMATION: A fragment from 1070 bp to 1600 bp of SEQ ID
      NO: 1 with deletion c 1079, deletion t 1111, deletion c 1155,
      deletion g 1183, deletion c 1185, substitution g for c 1536

<400> SEQUENCE: 9
gcgttaccca acttaatcgc cttgcagcac atccccttt cgccagctgg cgtaatagcg      60
aagaggcccg caacgaatcg cccttcccaa cagttgcgca agcctgaatg cgaatggaga    120
tccaattttt aagtgtntaa tgtgttaaac tactgattct aattgtttgt gtatnttaga    180
ttcacagtcc caaggctcat ttcaggcccc tcagtcctca cagtctgttc atgatcataa    240
tcagccatac cacatttgta gaggttttac ttgctttaaa aacctccca cacctccccc    300 tgaacctgaa acataaaatg aatgcaattg ttgttgttaa cttgtttatt gcagcttata    360
atggttacaa ataaagcaat agcatcacaa atttcacaaa taaagcattt ttttcactgc    420
attctagttg tggtttgtcc aaactcatca atgtatctta acgcgtaaat tgtaagcgtt    480
aatattttgt taaaattcgc gttaaatttt tgttaaatca gctcat                  526

<210> SEQ ID NO 10
<211> LENGTH: 523
<212> TYPE: DNA
<213> ORGANISM: Homo sapiens
<220> FEATURE:
<221> NAME/KEY: misc_feature
<222> LOCATION: (1)..(523)
<220> FEATURE:
<221> NAME/KEY: misc_feature
<222> LOCATION: (1)..(523)
<223> OTHER INFORMATION: A fragment from 1070 bp to 1600 bp of SEQ ID NO: 1 with deletion c 1071, deletion c 1079, deletion t 1111,
substitution a for c 1144, deletion a 1148, deletion c 1155,
deletion a 1173, deletion g 1183, deletion c 1185, substitution g
for c 1536

<400> SEQUENCE: 10

```
ggttacccaa cttaatcgcc ttgcagcaca tcccccttc gccagctggc gtaatagcga    60
agaggcccgc accgatcgcc cttcccaaca gttgcgcagc ctgaatgcga atggagatcc   120
aatttttaag tgtntaatgt gttaaactac tgattctaat tgtttgtgta tnttagattc   180
acagtcccaa ggctcatttc aggcccctca gtcctcacag tctgttcatg atcataatca   240
gccataccac atttgtagag gttttacttg ctttaaaaaa cctcccacac ctcccctga    300
acctgaaaca taaatgaat gcaattgttg ttgttaactt gtttattgca gcttataatg    360
gttacaaata aagcaatagc atcacaaatt tcacaaataa agcattttt tcactgcatt   420
ctagttgtgg tttgtccaaa ctcatcaatg tatcttaacg cgtaaattgt aagcgttaat   480
atttgttaa aattcgcgtt aaattttgt taaatcagct cat                       523
```

<210> SEQ ID NO 11
<211> LENGTH: 4853
<212> TYPE: DNA
<213> ORGANISM: Homo sapiens
<220> FEATURE:
<221> NAME/KEY: misc_feature
<222> LOCATION: (1)..(4853)
<223> OTHER INFORMATION: Modified sequence of SEQ ID NO: 1 with the
      following changes: deletion c 1079, deletion t 1111, substitution
      a for c 1144, deletion a 1148, deletion c 1155, deletion a 1173,
      deletion 1185, substitution g for c 1536

<400> SEQUENCE: 11

```
tatgccaagt acgcccccta ttgacgtcaa tgacggtaaa tggcccgcct ggcattatgc     60
ccagtacatg accttatggg actttcctac ttggcagtac atctacgtat tagtcatcgc    120
tattaccatg gtgatgcggt tttggcagta catcaatggg cgtggatagc ggtttgactc    180
acggggattt ccaagtctcc accccattga cgtcaatggg agtttgtttt ggcaccaaaa    240
tcaacgggac tttccaaaat gtcgtaacaa ctccgcccca ttgacgcaaa tgggcggtag    300
gcgtgtacgg tgggaggtct atataagcag agctggttta gtgaaccgtc agatccgcta    360
gtggatccaa agaattcggg cctccgaaac catgaacttt ctgctgtctt gggtgcattg    420
gagccttgcc ttgctgctct acctccacca tgccaagtgg tcccaggctg cacccatggc    480
agaaggagga gggcagaatc atcacgaagt ggtgaagttc atggatgtct atcagcgcag    540
ctactgccat ccaatcgaga ccctggtgga catcttccag gagtaccctg atgagatcga    600
gtacatcttc aagccatcct gtgtgccct gatgcgatgc gggggctgct gcaatgacga    660
gggcctggag tgtgtgccca ctgaggagtc aacatcacc atgcagatta tgcggatcaa    720
acctcaccaa ggccagcaca taggagagat gagcttccta cagcacaaca atgtgaatg    780
cagaccaaag aaagatagag caagacaaga aaatccctgt gggccttgct cagagcggag    840
aaagcatttg tttgtacaag atccgcagac gtgtaaatgt tcctgcaaaa acacagactc    900
gcgttgcaag gcgaggcagc ttgagttaaa cgaacgtact tgcagatgtg acaagccgag    960
gcggtgaccc gggtggggta ccaggtaagt gtacccaatt cgccctatag tgagtcgtat  1020
tacaattcac tggccgtcgt tttacaacgt cgtgactggg aaaaccctgg cgttacccaa  1080
cttaatcgcc ttgcagcaca tcccccttc gccagctggc gtaatagcga agaggcccgc  1140
accgatcgcc cttcccaaca gttgcgcagc ctgaatggcg aatggagatc caattttaa  1200
```

```
gtgtataatg tgttaaacta ctgattctaa ttgtttgtgt attttagatt cacagtccca    1260
aggctcattt caggcccctc agtcctcaca gtctgttcat gatcataatc agccatacca    1320
catttgtaga ggttttactt gctttaaaaa acctcccaca cctcccctg aacctgaaac     1380 ataaaatgaa tgcaattgtt gttgttaact tgtttattgc agcttataat ggttacaaat    1440
aaagcaatag catcacaaat ttcacaaata aagcattttt ttcactgcat tctagttgtg    1500
gtttgtccaa actcatcaat gtatcttaac gcgtaaattg taagcgttaa tattttgtta    1560
aaattcgcgt taaatttttg ttaaatcagc tcattttta accaataggc cgaaatcggc     1620
aaaatccctt ataaatcaaa agaatagacc gagatagggt tgagtgttgt tccagtttgg    1680
aacaagagtc cactattaaa gaacgtggac tccaacgtca aagggcgaaa accgtctat     1740 cagggcgatg gcccactacg tgaaccatca ccctaatcaa gttttttggg gtcgaggtgc    1800
cgtaaagcac taaatcggaa ccctaaaggg agccccgat ttagagcttg acggggaaag     1860
ccggcgaacg tggcgagaaa ggaagggaag aaagcgaaag gagcgggcgc tagggcgctg    1920
gcaagtgtag cggtcacgct gcgcgtaacc accacaccg ccgcgcttaa tgcgccgcta     1980
cagggcgcgt caggtggcac ttttcgggga aatgtgcgcg gaacccctat tgtttattt     2040 ttctaaatac attcaaatat gtatccgctc atgagacaat aaccctgata aatgcttcaa    2100
taatattgaa aaaggaagag tcctgaggcg gaaagaacca gctgtggaat gtgtgtcagt    2160
tagggtgtgg aaagtcccca ggctccccag caggcagaag tatgcaaagc atgcatctca    2220
attagtcagc aaccaggtgt ggaaagtccc caggctcccc agcaggcaga agtatgcaaa    2280
gcatgcatct caattagtca gcaaccatag tcccgcccct aactccgccc atcccgcccc    2340
taactccgcc cagttccgcc cattctccgc cccatggctg actaatttt tttatttatg     2400 cagaggccga ggccgcctcg gcctctgagc tattccagaa gtagtgagga ggcttttttg    2460
gaggcctagg cttttgcaaa gatcgatcaa gagacaggat gaggatcgtt tcgcatgatt    2520
gaacaagatg gattgcacgc aggttctccg gccgcttggg tggagaggct attcggctat    2580
gactgggcac aacagacaat cggctgctct gatgccgccg tgttccggct gtcagcgcag    2640
gggcgcccgg ttcttttgt caagaccgac ctgtccggtg ccctgaatga actgcaagac    2700
gaggcagcgc ggctatcgtg gctggccacg acgggcgttc cttgcgcagc tgtgctcgac    2760
gttgtcactg aagcgggaag ggactggctg ctattgggcg aagtgccggg gcaggatctc    2820
ctgtcatctc accttgctcc tgccgagaaa gtatccatca tggctgatgc aatgcggcgg    2880
ctgcatacgc ttgatccggc tacctgccca ttcgaccacc aagcgaaaca tcgcatcgag    2940
cgagcacgta ctcggatgga agccggtctt gtcgatcagg atgatctgga cgaagagcat    3000
caggggctcg cgccagccga actgttcgcc aggctcaagg cgagcatgcc cgacggcgag    3060
gatctcgtcg tgacccatgg cgatgcctgc ttgccgaata tcatggtgga aaatggccgc    3120
ttttctggat tcatcgactg tggccggctg ggtgtggcgg accgctatca ggacatagcg    3180
ttggctaccc gtgatattgc tgaagagctt ggcggcgaat gggctgaccg cttcctcgtg    3240
ctttacggta tcgccgctcc cgattcgcag cgcatcgcct tctatcgcct tcttgacgag    3300
ttcttctgag cgggactctg gggttcgaaa tgaccgacca agcgacgccc aacctgccat    3360
cacgagattt cgattccacc gccgccttct atgaaaggtt gggcttcgga atcgttttcc    3420
gggacgccgg ctgatgatc ctccagcgcg ggatctcat gctggagttc ttcgcccacc      3480 ctaggggag gctaactgaa acacggaagg agacaatacc ggaaggaacc cgcgctatga    3540
```

```
cggcaataaa aagacagaat aaaacgcacg gtgttgggtc gtttgttcat aaacgcgggg      3600
ttcggtccca gggctggcac tctgtcgata ccccaccgag accccattgg ggccaatacg      3660
cccgcgtttc ttccttttcc ccaccccacc ccccaagttc gggtgaaggc ccagggctcg      3720
cagccaacgt cggggcggca ggccctgcca tagcctcagg ttactcatat atactttaga      3780
ttgatttaaa acttcatttt taatttaaaa ggatctaggt gaagatcctt tttgataatc      3840
tcatgaccaa atcccttaa cgtgagtttt cgttccactg agcgtcagac cccgtagaaa       3900
agatcaaagg atcttcttga tccttttttt ttctgcgcgt aatctgctgc ttgcaaacaa      3960
aaaaaccacc gctaccagcg gtggtttgtt tgccggatca agagctacca actcttttc      4020 cgaaggtaac tggcttcagc agagcgcaga taccaaatac tgttcttcta gtgtagccgt      4080
agttaggcca ccacttcaag aactctgtag caccgcctac atacctcgct ctgctaatcc      4140
tgttaccagt ggctgctgcc agtggcgata agtcgtgtct taccgggttg gactcaagac      4200
gatagttacc ggataaggcg cagcggtcgg gctgaacggg gggttcgtgc acacagccca      4260
gcttggagcg aacgacctac accgaactga gatacctaca gcgtgagcta tgagaaagcg      4320
ccacgcttcc cgaagggaga aaggcggaca ggtatccggt aagcggcagg gtcggaacag      4380
gagagcgcac gagggagctt ccaggggaa acgcctggta tctttatagt cctgtcgggt       4440
ttcgccacct ctgacttgag cgtcgatttt tgtgatgctc gtcaggggg cggagcctat       4500 ggaaaaacgc cagcaacgcg gcctttttac ggttcctggc cttttgctgg cctttgctc       4560 acatgttctt tcctgcgtta tcccctgatt ctgtggataa ccgtattacc gccatgcatt      4620
agttattaat agtaatcaat tacggggtca ttagttcata gcccatatat ggagttccgc      4680
gttacataac ttacggtaaa tggcccgcct ggctgaccgc ccaacgaccc cgcccattg       4740 acgtcaataa tgacgtatgt tcccatagta acgccaatag ggactttcca ttgacgtcaa      4800
tgggtggagt atttacggta aactgcccac ttggcagtac atcaagtgta tca            4853
```

<210> SEQ ID NO 12
<211> LENGTH: 22
<212> TYPE: DNA
<213> ORGANISM: Artificial Sequence
<220> FEATURE:
<223> OTHER INFORMATION: VEGF forward primer

<400> SEQUENCE: 12
acattgttgg aagaagcagc cc                                              22

<210> SEQ ID NO 13
<211> LENGTH: 22
<212> TYPE: DNA
<213> ORGANISM: Artificial Sequence
<220> FEATURE:
<223> OTHER INFORMATION: VEGF reverse primer

<400> SEQUENCE: 13
aggaaggtca accactcaca ca                                              22

<210> SEQ ID NO 14
<211> LENGTH: 18
<212> TYPE: DNA
<213> ORGANISM: Artificial Sequence
<220> FEATURE:
<223> OTHER INFORMATION: Beta-actin forward primer

<400> SEQUENCE: 14
cgccccaggc accagggc                                                   18

```
<210> SEQ ID NO 15
<211> LENGTH: 18
<212> TYPE: DNA
<213> ORGANISM: Artificial Sequence
<220> FEATURE:
<223> OTHER INFORMATION: Beta-actin reverse primer

<400> SEQUENCE: 15
ggctggggtg ttgaaggt                                                  18
```

NUCLEOTIDE SEQUENCE AND PHARMACEUTICAL COMPOSITION BASED THEREON WITH PROLONGED VEGF TRANSGENE EXPRESSION

CROSS-REFERENCE TO RELATED APPLICATIONS

This is a divisional of application Ser. No. 15/070,239, filed Mar. 15, 2016, which claims priority to Russian Patent Application No. RU 2015119768 filed May 26, 2015, the contents of which are hereby incorporated herein by reference in its entirety. This application is related to U.S. application Ser. No. 14/423,532, published as U.S. Publication 2015/0335711 on Nov. 26, 2015, which is a national stage application of PCT/RU2013/000669, filed Aug. 2, 2013, which claims priority to Russian Patent Application No. RU 201237126, filed Aug. 31, 2012, of which all of the contents are hereby incorporated herein by reference in their entireties.

BACKGROUND

Field of the Disclosure

The present invention relates to bioengineering, more particularly, to compositions for gene therapy with Vascular Endothelial Growth Factor (VEGF) having a high stability and prolonged and reliable VEGF transgene expression and a method for extending the lifetime of a transgene mRNA in a mammalian cell transfected with the composition.

Description of the Related Art

VEGF and its Biological Role

VEGF is a family of biologically active proteins first isolated by J. Folkman et al. in 1971 [8] that are produced by the cells of most or all bodily tissues, including epithelial tissue. The VEFG family is considered to represent major autocrine and paracrine factors for regulation of vasculogenesis, angiogenesis (VEGF-A, VEGF-B; PIGF) and lymphogenesis (VEGF-C, VEGF-D).

The formation of vasculature during human postnatal development of a human is mostly influenced by all VEGF isoforms including VEGF-A isoforms 121, 145, 148, 165, 183, 189 and 206 [9].

Three types of VEGF receptors have been identified. Types 1 and 2 are involved in angiogenesis and type 3 is involved in the formation of lymphatic vessels. At the same time, while type 1 receptor has a higher affinity to the VEGF, its tyrosine kinase activity is much lower than that of type 2 receptor, which is regarded as one of the regulatory mechanisms preventing an excessive VEGF activity. Accordingly, it is through type 2 receptor that the VEGF effects are normally realized [10, 11].

Upon VEGF interaction with a specific type 2 receptor, autophosphorylation of its intracellular tyrosine sites (Y951, 1054, 1059, 1175, 1214) of kinase and carboxyterminal domains takes place [11]. This in turn activates a number of intracellular proteins, such as phospholipases Cγ, Cβ3, SRK, NCK, SHB, SCK adaptor proteins and others, which comprise first units of the signal transduction complex cascades modifying the morphofunctional state of the target (mostly endothelial) cells. In particular, phospholipase Cγ hydrolyzes the $PIP_2$ membrane phospholipid resulting in the formation of diacylated glycerol and inositol-1,4,5-triphosphate increasing the intracellular content of calcium, which together activate protein kinase C, which in turn triggers sequential activation of the RAS-ERK signal path leading to induction of mitosis. As a result, the proliferative activity of endothelial cells becomes higher [10].

Phospholipase Cβ3 is involved in polymerization of actin and in the formation of stress fibrils enabling migration and motor performance of cells in general [12]. VEGF blocks apoptosis via activation of the "phosphoinositide-3-kinase—protein kinase B" (PI3K/AKT) signal path, inhibiting caspases 3, 7, and 9 and thereby increasing cell survival rate.

In addition, with the help of calcium ions, the PI3K/AKT axis modulates the activity of endothelial NO-synthase, which is accompanied by the increased NO production and increased vascular permeability being a necessary part of angiogenesis (FIG. 3) [13, 14]. Therefore, VEGF, via the specific type 2 receptor, induces activation, migration and differentiation of endotheliocytes and their precursor cells, increases cell survival rate, which in combination with the modulation of intercellular interactions and the increase of vascular permeability provide a prerequisite for the formation of capillary-like constructs followed by their remodeling into "mature" vessels [10-16].

Considering the role of VEGF as a key angiogenic factor, variations of the genes encoding VEGF are used for developing gene constructs suitable for treating patients with cardiovascular diseases of ischemic genesis [17, 18]. In addition, a non-specific angiogenic effect of such preparations for gene therapy may have a positive influence in case of other pathological conditions requiring activation of a reparative process, e.g., injury of peripheral nerves [19], diabetic foot syndrome [20], amyotrophic lateral sclerosis [21], injuries of skeleton bones [22, 23] and others.

As to bone tissue, both in case of primary and secondary osteohistogenesis, precisely the vessels growing into loose fibrous connective or cartilaginous tissue create required conditions for differentiation of the resident cells in the osteoblastic direction as well as for migration of cambial reserves (perivascularly and with the blood flow). Apart from the angiogenesis-mediated influence, VEGF also has a direct stimulating effect on osteoblastic programmed differentiation cells which not only produce VEGF [24] but also express its types 1 and 2 receptors both during embryogenesis [25] and postnatal development [26]. It has been shown that VEGF enables a considerable increase (up to 70%) in proliferation of osseous tissue cambial cells and also activates migration of osteogenic cells according to a VEGF concentration gradient [27-29].

In the past few years, a principally different mechanism referred to as "intracrinic" has been identified in addition to the canonical receptor mechanism of the VEGF action. These findings have been confirmed by the showing that progenitor cells committed in the osteoblastic direction (expressing Osx) synthesize VEGF not only "for exportation" but also to enable its own differentiation in the osteoblastic direction [30].

VEGF has a wide spectrum of action on the endothelial and mesenchymal cell lines. Although a major biological effect of VEGF is associated with induction of the formation of blood and lymphatic vessels, other mechanisms of direct action on the cells of various programmed differentiations via receptors and intracrinic mechanisms may be also characteristic for VEGF. However, more convenient and effective ways of expressing VEGF for treating subjects with diseases, disorders or conditions in need of VEGF are desired.

Conventional Preparations for Gene Therapy

Pharmaceutical preparations for gene therapy comprising nucleic acid constructs and genes expressing useful products, such as vectors containing one or more polynucleotides encoding a therapeutic protein (e.g., VEGF), are becoming of ever greater importance in modern medicine. Until now, five such preparations have been already registered and introduced in clinical practice and hundreds are undergoing experimental studies and clinical trials. A total number of gene therapy clinical trials conducted since 1989 exceeds 1,900 [1]. One of the five registered preparations for gene therapy, Neovasculgen, has been developed and introduced in clinical practice in Russia (Reg. Certificate No. LP-000671 of Sep. 28, 2011) and Ukraine (Reg. Certificate No. 899/13300200000 of Jan. 25, 2013) by the present Applicants. Other gene therapy medicaments are currently under development.

However, existing compositions for gene therapy suffer from a variety of technical problems. While preparations using plasmid vectors to carry a gene encoding a therapeutic protein are considered among the safest types of gene constructs, the efficacy of a gene therapy composition is a function of transformation efficiency, stability of a vector once transformed into a cell, transcription of RNA, stability of transcribed mRNA encoding the therapeutic protein, and activity and stability of the expressed therapeutic protein.

The Neovasculgen gene therapy preparation employs a plasmid DNA vector in combination with a polynucleotide encoding VEGF, a therapeutic protein. However, in order for such gene therapy to be effective a sufficient number of transgenes must enter target cells and be expressed. However, a recognized problem with gene therapy employing plasmid vectors is the low transfection efficiency. Only 1 to 2% of the total number of transgenes reach and/or are expressed by target cells [2]. The low transfection efficiency impacts the amount of therapeutic protein that can be expressed after conventional gene therapy using plasmid vectors because the total number of transfected host cells directly affects the total amount of therapeutic protein produced. On the other hand, for safety and to avoid side-effects it is desirable to minimize the amount of transgenic DNA administered to a subject because administration of too high an amount of transgenic nucleic acid can result in toxicity, inflammatory responses, and in problems with transgene control and targeting.

Consequently, and particularly with respect to gene therapies using plasmids having low transfection efficiencies, methods for increasing the amount of a therapeutic protein encoded by transgenes while decreasing the administered dose of transgenic polynucleotides are of great interest.

There are two principle approaches to increasing the amount of a therapeutic protein expressed by a transgene: (i) modifying the transgenic nucleic acid to improve its uptake by host cells (increasing transfection efficiency) and (ii) increasing the amount of therapeutic protein expressed by host cells that have been transformed with a transgenic nucleic acid. To date there have been significant problems with both approaches.

To increase transfection efficiency, a number of genetic, physical and chemical methods have been proposed. Many or most of these conventional laboratory methods of increasing transfection efficiency, are not generally suitable for gene therapy in the clinic. For example, in the therapeutic context, use of non-plasmid vectors, such as viral vectors, is associated with a significant risk of genetic disruption to a host cell when viral vectors unpredictably integrate into the host cell genome. Physical methods such as direct injection or bombardment of a host cell with particles containing a transgene require special equipment and are not feasible, convenient or safe in a clinical setting. Chemical methods, such as use of liposomes, dendrimers or other chemical agents to facilitate uptake of a transgene by a host cell often result in only transient expression of the transgene and require comingling of the transgene with additional chemical components that create an additional risk when administered to a subject.

The second approached mentioned above seeks to prolong the lifetime of mRNA or other transcription product of a transgene that has entered a host cell, resulting in an increase in the number of times or cycles that mRNA encoding a therapeutic polypeptide is translated, and an overall increase in the amount of the therapeutic product produced by a transfected cell. How mRNA can be stabilized inside the cell to transcribe more of a protein of interest is not completely understood and the cell may require a coordinated system of mRNA degradation and stabilization for normal functioning. According to a number of researchers, some pathological conditions of inflammatory or oncologic genesis may be associated with the post-transcriptional deregulation leading either to insufficient or excessive production of growth factors, oncogenes and other biologically active substances [4]. Thus, a safe and effective method for modulating the mRNA lifetime should attempt to minimize intervention as a way of reducing a risk of disrupting the normal cell functioning.

The prior research of mRNA lifetime has identified some factors including 3'-UTR sequences and regulatory molecules that modulate mRNA lifetime. Regulatory molecules include RNA-binding proteins and regulatory RNAs, such as micro RNAs and long non-coding RNAs. Such regulatory molecules can act via binding to a 3'untranslated region ("3'-UTR") of protein-coding mRNA. Regulatory molecules once bound to a 3'UTR can destabilize or stabilize mRNA encoding a protein of interest. A number of regulator molecules, such as adenine-uridine-rich-("AU-rich") elements, RNA-binding protein 1 (AUF1), tristetraprolin (TTP), KH-type splicing regulatory protein (KSRP) can induce mRNA degradation by binding to 3'UTR specific sites. In contrast, regulatory elements such as polyadenylate-binding protein-interacting protein 2 (PAIP2) stabilize mRNA [3, 4]. The binding of regulator factors to mRNA is only one aspect of the system of regulating mRNA lifetime.

Methods for modifying a 3'UTR nucleotide sequence or a destabilizing element in a 3'UTR were known. These include use of site-specific mutagenesis to modify these sequences. However, to date, it has been unknown whether particular mutations to the 3'-UTR sequence of VEGF would permit one to prolong the lifetime of mRNA encoding VEGF without reducing translation of VEGF or otherwise diminishing expression of VEGF [3]. This unpredictability is due, in part, mRNA isoforms differing in their 3'UTR nucleotide sequences which can vary within a wide range due to alternative splicing, differential polyadenylation and other intracellular mechanisms. Moreover, a composition of a 3'UTR destabilizing (or stabilizing) element also qualitatively and quantitatively depends on its associated nucleic acid coding region. Furthermore, modeling of the effects of particular modifications on mRNA lifetime has been difficult or impossible because the 3'UTR plays other roles in cellular physiology and metabolism. Thus, modification of a 3'UTR can unpredictably affect other cellular processes necessary for stable and prolonged transcription of mRNA and stable, prolonged and active expression of the protein encoded by the mRNA. Consequently, whether a particular modification would increase or decrease mRNA lifetime of mRNA encoding VEGF has previously been unknown.

Despite all difficulties and insufficiently studied issues of the determination or "programming" the mRNA lifetime via changing a 3'UTR sequence, attempts are still being made to empirically select such changes in respective regions of specific gene construct variants that would enhance mRNA stability without negatively affecting its functionality. In particular, a method for increasing transgene production by substituting the AU-rich element sequence presented by AUUUA with other variants and combinations thereof limited to AUGUA, AUAUA, GUGUG, AGGGA, GAGAG, has been known [5]. However, the above sequence of the destabilizing element in 3'UTR is not specific to for all genes (described by most of researchers for G-CSF) and, on the other hand, it does not exhaust a list of the destabilizing elements and, therefore, the mRNA lifetime extension may be diminished. A special 3'UTR sequence of the erythropoietin gene has also been developed that provides prolonged production of the transgene being a part of plasmid DNA. The sequence is strictly specific and has a length of 100 nucleotides [6].

Methods for elimination of specific 3'UTR sequences that are responsible for binding to various microRNAs and that induce mRNA degradation have been also described [7]. However, most of the proposed changes in the 3'UTR sequence relate to lengthy deletions or substitutions, which are inevitably associated with a risk of negative effects on the mRNA metabolism. In addition, proposed solutions are highly dependent on the gene coding region so that some of such solutions are inapplicable while other solutions are insufficiently efficient for a VEGF gene and for extension of the lifetime of its transcription product.

In view of the importance of treating diseases, disorders or conditions that would benefit from transgenic administration of VEGF, the inventors have diligently investigated and now found ways to modify the 3'UTR of VEGF in a way that minimizes a risk of disrupting mRNA regulation in a host cell, while providing for prolonged expression of active VEGF. Moreover, as shown herein, these modifications are effective in a variety of cells including HEK293 human cell line, multipotent mesenchymal stromal cells, and human fibroblasts. To provide this therapy, the inventors diligently studied ways to avoid the problems associated with existing gene therapies, such as therapies that depend on plasmid vectors that have low transfection efficiencies.

The inventors provide herewith a safe and effective way of introducing DNA encoding VEGF into host cells that prolongs VEGF-transgene expression for use in medicinal preparations and gene-activated medical products intended for treating patients not only with cardiovascular diseases but also with other pathology, wherein local increase in the VEGF level within the affected area would enhance the reparative process.

SUMMARY OF THE INVENTION

Engineered transgenes encoding VEGF and vectors and host cells containing these transgenes are disclosed. These transgenes contain targeted modifications to the 3'UTR sequence of mRNA encoding VEGF which enhance or prolong production of mRNA encoding VEGF and thus permit safer and more efficacious VEGF gene therapy. Examples of these modifications to the 3'UTR segment of VEGF mRNA are depicted in Table 1 and their effects on prolonging mRNA life in host cells are shown in FIG. 1.

One object of the present invention is to provide a method for extending the lifetime of mRNA encoding vascular endothelial growth factor (VEGF) in a host cell comprising performing at least one pointwise single deletion of guanine or adenosine, or performing at least one pointwise single substitution of guanine or adenosine with cytosine, in an 3'-untranslated region of a vegf gene to produce mutant mRNA; transforming said mutant mRNA into a host cell; determining lifetime of said mutant mRNA in the host cell; and selecting mutant mRNA that increases the lifetime of mRNA encoding VEGF compared to control non-mutated mRNA encoding VEGF.

In one embodiment, mutant mRNA increases the amount of VEGF expressed compared to the amount expressed by the control non-mutated mRNA.

In another embodiment, mRNA encoding VEGF is from isoforms VEGF-121, VEGF-145, VEGF-148, VEGF-165, and VEGF-183, VEGF-189, or VEGF-206.

In a different embodiment, the host cell may be a mammalian cell. In yet another embodiment, the host cell is obtained from a subject in need of increased expression of VEGF.

A further object of the present invention is to provide an engineered polynucleotide comprising a modified 3'-UTR sequence from a VEGF gene that comprises at least one nucleotide sequence modification to a native 3'-UTR sequence of a VEGF gene and a structural gene encoding VEGF, wherein when said polynucleotide is transformed into and transcribed by cells, its transcription product has an extended lifetime compared to the transcription product of the polynucleotide described by SEQ ID NO: 1 when transformed into cells.

In one embodiment, at least one nucleotide sequence modification comprises at least one substitution to the 3'-UTR sequence of a native VEGF gene.

In another embodiment, at least one nucleotide sequence modification comprises at least one addition or deletion to the 3'-UTR sequence of a native VEGF gene.

In another embodiment, the engineered polynucleotide comprises at least one nucleotide sequence modification selected from the group consisting of C-deletion at position 1071, C-deletion at position 1079, T-deletion at position 1111, A/C-substitution at position 1144, A-deletion at position 1148, C-deletion at position 1155, A-deletion at position 1173, G-deletion at position 1083, A-deletion at position 1185, and G/C-substitution at position 1536; wherein said positions correspond to those described by SEQ ID NO: 1.

The polynucleotide may comprise or consist of SEQ ID NO: 11.

A further object of the present invention is to provide a vector or polynucleotide construct comprising the engineered polynucleotide. The vector or polynucleotide may be a plasmid. The vector or polynucleotide may comprise the polynucleotide sequence of SEQ ID NO: 11.

A further object of the present invention is to provide a pharmaceutical composition comprising the vector or polynucleotide construct in the form suitable for administration to a mammalian subject, and, optionally, at least one cryoprotectant and/or pH stabilizer.

A further object of the present invention is to provide a cell that has been transformed or transfected with the vector or polynucleotide construct. The cell may be autologous to or obtained from a subject receiving said cell. Alternatively, such a cell may be matched for histocompatibility with a subject. Optionally, such a cell may be transformed ex vivo or in vitro and then reintroduced into a subject.

A further object of the present invention is to provide a method for treating a subject in need of VEGF comprising administering the vector or polynucleotide construction to said subject. In one embodiment, the subject is in need of regeneration of a connective, neural, muscular, osseous or cardiovascular tissue.

A further object of the present invention is to provide an mRNA of the vector or polynucleotide construct, comprising the 3'-untranslated region comprising at least one deletion and/or substitution of at least one single nucleotide in the vector or polynucleotide construct according.

In one embodiment, cells may be HEK293 cells.

In another embodiment, the engineered polynucleotide is transformed into and transcribed by a HEK293 cell, its transcription product has an extended lifetime compared to the transcription product of the polynucleotide described by SEQ ID NO:1 when transformed into an otherwise identical HEK293 cell These and other objects of the present invention will become more apparent in conjunction with the following detailed description of the preferred embodiments, either alone or in combinations thereof.

BRIEF DESCRIPTION OF THE DRAWINGS

The patent or application file contains at least one drawing executed in color. Copies of this patent or patent application publication with color drawing(s) will be provided by the office upon request and payment of the necessary fee.

A more complete appreciation of an object of the present disclosure and many of the advantages thereof will be readily obtained as the same becomes better understood by reference to the following detailed description when considered in connection with the accompanying drawings which are described below.

FIG. 2, trace "A" depicts accumulation from original gene construct (SEQ ID NO:1); FIG. 2, trace "B" depicts accumulation from an engineered gene construct (SEQ ID NO:11). The results are presented as a multiple magnification in comparison with the mRNA production level in the endogenous VEGF.

FIG. 3, bar "A" (first bar in each set) depicts endogenous VEGF production from a non-transfected cell culture; FIG. 3, bar "B" (second bar) depicts VEGF production from an original gene construct (SEQ ID NO:1); FIG. 3, bar "C" (third bar) describes VEFG production from the engineered gene construct (SEQ ID NO:11).

FIG. 4, lane B (second lane) depicts protein from original gene construct (SEQ ID NO: 1); FIG. 4, lane C (third lane) depicts protein from a control, non-transfected cell culture.

FIG. 8A—calcium phosphate with plasmid DNA SEQ ID NO: 11, FIG. 8B—calcium phosphate without plasmid DNA.

DETAILED DESCRIPTION OF THE EMBODIMENTS

Figure 1:
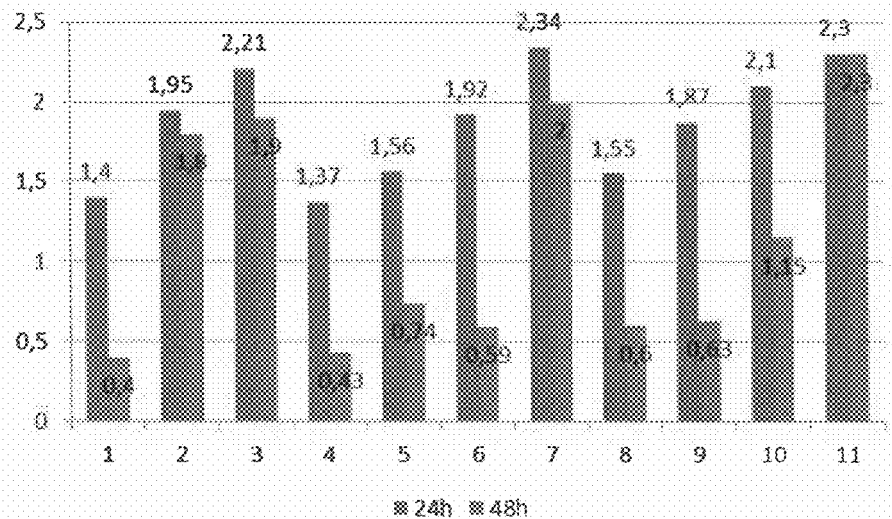
FIG. 1 shows mRNA production (accumulation) by cell cultures transfected with variant gene constructs. Samples 1 through 11 along the X-axis respectively refer to the polynucleotides of SEQ ID NOS: 1 through 11. The first bar in each set shows the mRNA production (accumulation) at 24 hrs; the second bar that produced (accumulated) at 48 hrs.

The inventor has previously engineered the gene construct described by SEQ ID NO:1. As shown in FIG. 1, this construct was produced using methods of site-specific mutagenesis and quantitative PCR analysis of RNA molecules in a cell. The inventor has also studied constructs with different changes in the 3'UTR nucleotide sequence of the therapeutic VEGF gene in comparison with the original gene construct (SEQ ID NO:1).

Table 1 below shows exemplary influences of certain changes. As can be seen herein, certain deletions or substitutions, for example, deletion of C 1079, in the nucleotide sequence positively affect mRNA lifetime, while other changes had no effect (for example, deletion of C 1100) or led to a decrease in mRNA lifetime (for example, deletion of C 1090).

At the same time, the mRNA lifetime of the VEGF gene varied by more than 6 hours on average with the mRNA average lifetime being 6 hours (deletion of C1079—increase; deletion of C1090—decrease).

All changes having a positive effect were used for developing a number of gene construct variants with four to ten "positive" mutations in various combinations, i.e., differing in the nucleotide sequence in the interval of 1070-1600 nt (SEQ ID NOS: 2-11).

Based on these findings, the inventor has selected and synthesized an original 3'UTR terminal part of the VEGF gene, which in combination with the gene coding region enabled an increase by 70% in the gene transcript lifetime (SEQ ID NO: 11), and wherein certain mutations having most positive effects on mRNA in the aggregate were brought together, deletion of C 1079, deletion of T 1111, substitution of A with C 1144, deletion of A 1148, deletion of C 1155, deletion of A 1173, deletion of C 1185, and substitution of G with C 1536. The resulting gene construct variant is characterized by a maximum mRNA lifetime and, accordingly, the highest total production of a VEGF protein among other variants, which exceeds the production typical for the original gene construct (SEQ ID NO: 1).

Based on the developed engineered gene constructs and adjuvants enabling cryoprotection, pH stabilization and preparation of an isotonic solution for injections, pharmaceutical compositions with a marked angiogenic activity were produced. Resulting pharmaceutical compositions are suitable for treatment of diseases and pathological conditions that require stimulation of angiogenesis (tissue ischemia) or reparative tissue regeneration which may be accomplished through activation of angiogenesis (synthesis of continuity of peripheral nerves, bones, etc.)

For production of the developed pharmaceutical compositions, a bacterial (*E. coli*) producer strain was created for the gene construct having the nucleotide sequence of SEQ ID NO:11, deposited at the All-Russian Collection of Microorganisms at 1 first Dorozhniy proezd, Moscow, Russia 117545, in accordance with the Budapest Treaty on the International Recognition of the Deposit of Microorganisms for the Purposes of Patent Procedure (strain deposit number VKM B-2967D).

The site-specific mutagenesis of the VEGF gene 3'UTR was accomplished using the QuikChange® Lightning Site-Directed Mutagenesis Kit (Agilent Technologies, USA) according to the manufacturer's instructions.

The site-specific mutagenesis of the original plasmid DNA (SEQ ID NO:1) resulted in variant changes in the 3'UTR of the VEGF gene. The resulting plasmid DNA variant with the VEGF gene differing in the 3'UTR sequence were used for transfection of HEK293 cell lines followed by determination of the dynamics of accumulation of the gene construct expression product, i.e., mRNA of the VEGF gene.

TABLE 1

Examples of certain changes in the nucleotide sequence and their influence on the mRNA lifetime

| Position* | Change | Original nucleotide | Corrected nucleotide | Influence on the mRNA lifetime |
|---|---|---|---|---|
| 1071 | Deletion | C | — | increase |
| 1079 | Deletion | C | — | increase |
| 1090 | Deletion | C | — | decrease |
| 1100 | Deletion | C | — | no influence |
| 1111 | Deletion | T | — | increase |
| 1113 | Substitution | G | C | no influence |
| 1144 | Substitution | A | C | increase |
| 1146 | Deletion | G | — | decrease |
| 1148 | Deletion | A | — | increase |
| 1150 | Deletion | C | — | no influence |
| 1155 | Deletion | C | — | increase |
| 1158 | Deletion | C | — | decrease |
| 1173 | Deletion | A | — | increase |
| 1175 | Deletion | C | — | decrease |
| 1183 | Deletion | G | — | increase |
| 1184 | Deletion | C | — | decrease |
| 1185 | Deletion | C | — | increase |
| 1187 | Substitution | A | C | no influence |
| 1536 | Substitution | G | C | increase |

*Note:
the nucleotide numbering is given according to the original reference sequence of the gene construct having the nucleotide sequence of SEQ ID NO: 1.

$2 \times 10^5$ of HEK293 cells were placed onto the wells of a 6-well plate containing a DMEM/F-12 cultural medium with added 10% FBS. After the attachment of the cells, 10 µg of one of the obtained plasmid DNA variants was added to the cultural medium (in 100 µl of water for injection). As a negative control, 100 µl of water for injection without plasmid DNA was used so that the production level of the endogenous VEGF mRNA could be assessed. In order to determine a VEGF gene expression level, the real-time PCR was accomplished for isolating the total RNA from the cells 6, 12, 24, 36 and 48 hours after transfection by a column-based method using PureLink® RNA Mini Kit (Invitrogen, USA) according to the manufacturer's instruction. Briefly, the precipitated cells were carefully lysed in 350 µl of a lytic buffer in the presence of 1% β-mercaptoethanol. An equal volume of 70% ethanol was added, vortexed and transferred onto the columns, centrifuged for 1 min at 12,400 rpm. The centrifuge liquid was drained. 600 µl of washing solution 1 was added onto the membrane, centrifuged for 15 sec at 12,400 rpm, and the liquid was removed. 500 µl of washing solution 2 was added onto the membrane, centrifuged under the same conditions, and the liquid was removed. The washing procedure was repeated using washing solution 2. The columns were transferred into new vials and centrifuged for 1 min at 12,400 rpm. The columns were transferred into vials to collect RNA. 15 µl of water without RNAs was added directly onto the membrane, incubated for 1 min at room temperature, and centrifuged for 90 sec at 12,400 rpm. The samples were kept at −80° C. until further use. Then, a first chain of complementary DNA was synthesized using reagents available from Promega (USA). The expression level of the target genes (in moles) was determined as compared to the expression of the β-actin housekeeping gene using a kit for accomplishing a real-time PCR in the presence of SYBR® Green I (an asymmetrical cyanine dye; Zipper H; Brunner H; Bernhagen J; Vitzthum F (2004). "Investigations on DNA intercalation and surface binding by SYBR Green I, its structure determination and methodological implications". Nucleic Acids Research, 32(12):e103 (Jul. 12, 2004)) and a ROX® reference colorant (inert dye which fluorescence does not change during the reaction) (Syntol, Russia). FIG. 1 shows an example of the nucleotide substitution that provides an increase in the mRNA lifetime.

Reverse Transcription Reaction:
1) on ice: 2.5 µl of Random Hexamer was added to 10 µl of RNA and incubated for 5 min at 70° C.;
2) ice was removed;
3) drops were settled;
4) a mixture was prepared for each sample, comprising:
5 µl of MMLV 5× reverse transcriptase buffer
1.25 dNTP
1.25 RNase inhibitor
1 µl of MMLV transcriptase
4 µl of H$_2$O
5) 12.5 µl of the mixture was added to each vial and incubated for 1 hour at 37° C.;
6) reactions were stopped by incubation at 75° C. for 5 min.

All complementary DNA samples were kept at −80° C.

The forward and reverse primers for VEGF and β-actin genes were used to accomplish the real-time PCR (Table 2). The real-time PCR reaction mixture was used in the presence of SYBR® Green I according to the manufacturer's instructions. The measurements were carried out using CFX90 Touch™ Real-time PCR Detection System.

TABLE 2

| | PCR Primers | |
|---|---|---|
| Gene | Forward primer | Reverse primer |
| VEGF | ACATTGTTGGAAGAAGCAGC CC (SEQ ID NO: 12) | AGGAAGGTCAACCACTCACA CA (SEQ ID NO: 13) |
| β-actin | CGCCCCAGGCACCAGGGC (SEQ ID NO: 14) | GGCTGGGGTGTTGAAGGT (SEQ ID NO: 15) |

As a result, mutations were identified positively influencing mRNA lifetime (deletion of C 1071, deletion of C 1079, deletion of T 1111, substitution of A for C 1144, deletion of A 1148, deletion of C 1155, deletion of A 1173, deletion of G 1183, deletion of C 1185, substitution of G for C 1536 and others). The changes in various combinations of 4-10 mutations were brought together into synthetic constructs including a coding region of the VEGF gene and 3'UTR, and engineered in relation to the VEGF gene. Some of the obtained variants are presented by SEQ ID NOS: 2-11. In order to select the most optimal variant from the developed gene constructs, a comparative study was carried out during which the accumulation dynamics of mRNA by the transfected cells was determined by the real-time PCR, as discussed above. FIG. 1 shows ten gene constructs that showed maximum multiplicity of increase of the mRNA concentration at 24 and 48 hours after transfection.

As shown in the graph, in certain cases combinations of several mutations each separately having a positive effect on the mRNA lifetime produced no significant increase in the accumulation of mRNA as compared to the original gene construct (SEQ ID NO: 1). For the gene constructs characterized by an increased mRNA lifetime, the lack of a drop in the concentration was observed only for SEQ ID NO:11 while in other cases, the mRNA level had dropped 48 hours after transfection as compared to the level at 24 hours. This gene construct was selected as the most promising and was subjected to further comparative studies.

Figure 2:
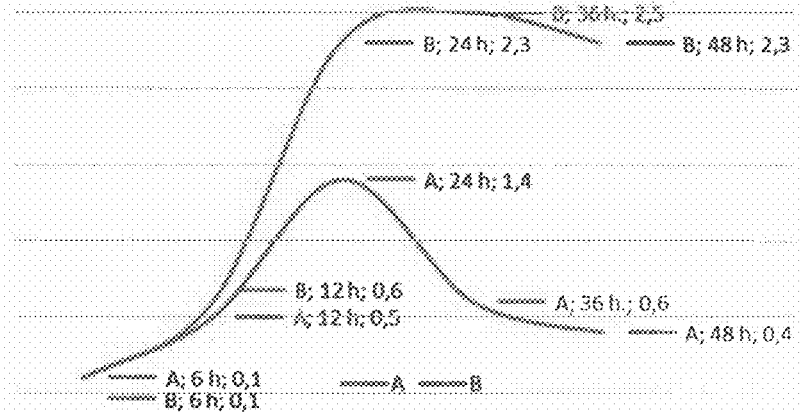
FIG. 2 shows dynamics of the mRNA production (accumulation) in the VEGF gene by a transfected cell culture over a 48 hr period.

FIG. 2 shows a result of the real-time PCR for the sequence of SEQ ID NO:11 in comparison to the non-modified sequence of SEQ ID NO:1. As can been seen in the graph, as early as after 12 hours, the modified construct had the level of mRNA of the VEGF gene exceeding the parameter value in the control group using original plasmid DNA for transfection. Importantly, the dynamics of increase in the mRNA concentration in both groups has coincided with the peak value at 24 hours after transfection. However, a gradual decrease in the mRNA level associated with rapid biodegradation of molecules was observed only for the original gene construct whereas a "plateau" phase lasting at least 6 hours and followed by a smooth decrease in the mRNA concentration was observed for the modified construct (SEQ ID NO:11). At the same time, a difference between the groups in terms of this value was 190% at the latest time point.

Figure 3:
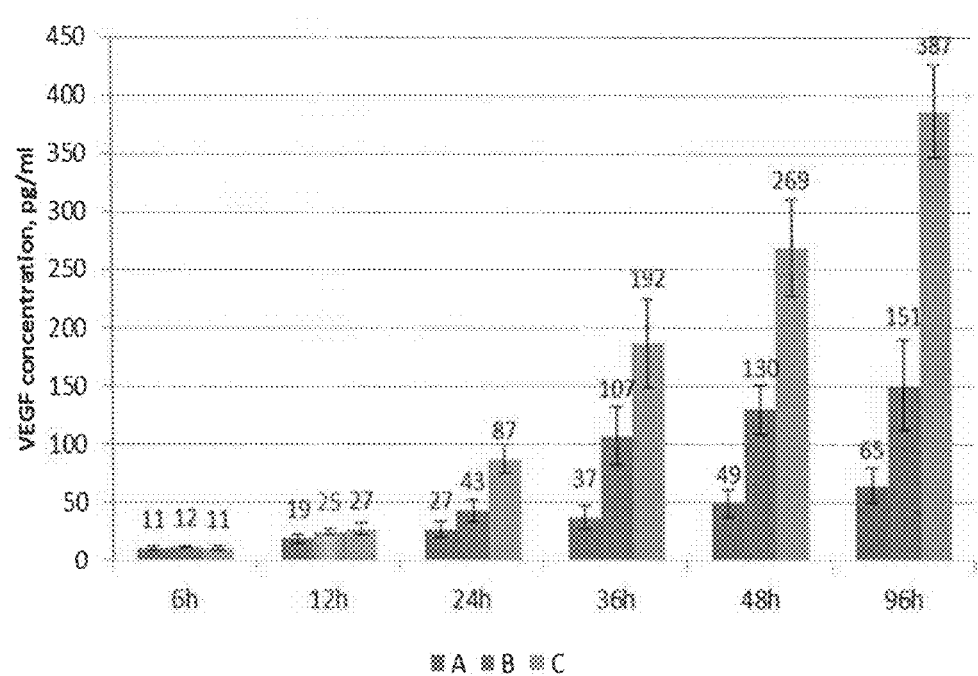
FIG. 3 shows dynamics of the mRNA production in the VEGF gene by a transfected cell culture.

The developed plasmid DNA carrying a VEGF gene was studied in vitro in order to quantify the production of a VEGF protein by HEK273 cells. The concentration of the therapeutic protein in a cultural medium was determined using ELISA 6, 12, 24, 48, 72 and 96 hours after cell transfection. The accumulated concentration of the therapeutic protein in the cultural medium for the cells transfected with the gene construct was far higher than the parameter value in the control groups including the groups with alternative gene constructs characterized by a non-modified 3'UTR sequence of the VEGF gene and standard lifetime of transgene mRNA (FIG. 3). Importantly, the maximum increase in the VEGF concentration in the cultural medium for both groups of transfected cells (2.3-2.4 times) was observed 36 hours after the experiment had started, which had agreed with the real-time PCR data showing a peak concentration of mRNA in gene constructs at 24 hours. Later on, while the concentration of the VEGF protein in the medium of the cells transfected with the modified gene construct continued to increase at a high rate, the increase significantly slowed down in the group with the original plasmid DNA and slightly exceeded the increase in the control group (non-transfected culture).

Figure 4:
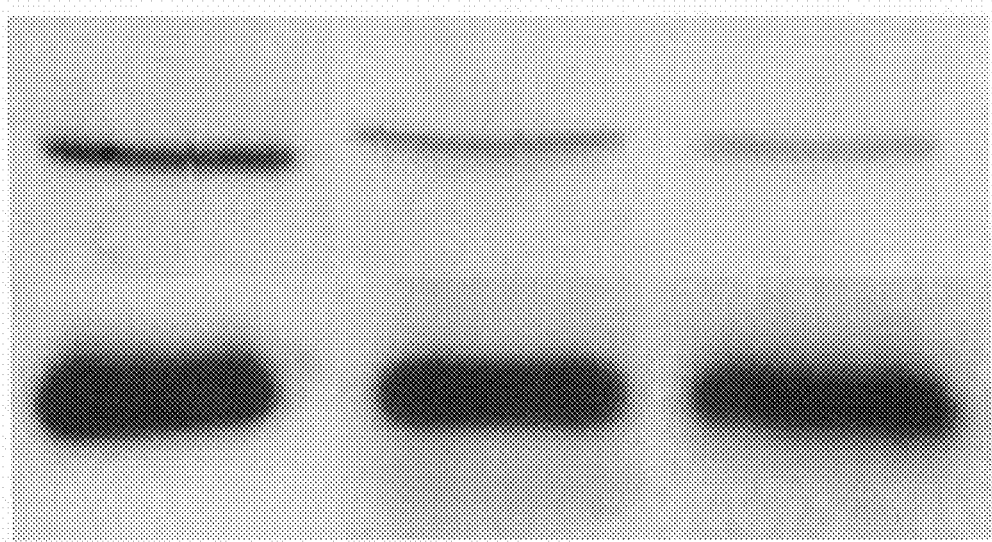
FIG. 4 depicts Western blot gel-resolved VEFG proteins isolated from cell cultures transfected with gene constructs on day 4 after transfection (normalized to β-actin) FIG. 4, lane "A" (first lane) depicts protein from the engineered gene construct (SEQ ID NO: 11)

While the accumulated concentration of a VEGF protein measured in a cultural medium makes it possible to estimate its production by the cells and to quantify its increase at each control time point, it does not allow the intracellular concentration of the protein to be evaluated at each time point. At the same time, it is particularly important for the integrated assessment of the mRNA lifetime in gene constructs to determine a level of a VEGF protein in the cells at the latest time points of observation. In this connection, the cells after 4 days of cultivation were subjected to a Western blotting analysis according to a standard technique using anti-VEGF antibodies. The protein concentration was found to be the highest in the cell lysate transfected with the modified gene construct having the nucleotide sequence of SEQ ID NO:11 (FIG. 4). At the same time, a protein level for the cells transfected with the original construct was insignificantly higher than the endogenous concentration (control) at this stage of observation.

Moreover, the conditioned cell medium transfected with the modified gene constructs was characterized by a significantly higher angiogenic activity as determined by a test using a HUVEC tube formation assay.

Comparing the findings of the conducted studies, it has been concluded that mRNA in the modified gene construct (SEQ ID NO:11) was characterized by a longer lifetime leading to more prolonged production of the VEGF therapeutic protein at high concentrations up to the latest points of observation. In contrast, the original gene construct was characterized by a lower mRNA stability and a short and less marked biological effect.

Therefore, a technical effect described in the present application includes an increase of the total production of a therapeutic protein due to the increased mRNA lifetime achieved by identifying certain 3'UTR sequences of a VEGF gene. It has been surprisingly found that substitution of one nucleotide in the target region has such a marked effect on the mRNA lifetime and, therefore, on the production of the therapeutic protein. In all previous studies in the field, different changes were carried out involving far more nucleotides. Considering that functionality of each site in mRNA's 3'UTR is insufficiently studied, precisely minimal, pointwise changes are favorable in terms of safety and leveling the influence on other aspects of the mRNA metabolism as long as such changes allow a necessary effect to be achieved. It is important to note that the length of the 3'UTR sequence in the VEGF gene is at least 250 nucleotides so that the total number of only single pointwise mutations in the form of substitution of one nucleotide with another is at least 750. Taking into account other possible variants of changes (deletions, duplications, insertions) and also allowing for the involvement of more than one site, the number of gene construct variants differing in the 3'UTR of a VEGF gene amounts to hundreds of thousands. The identification of a number of variants of changes in the sequence resulting in the increased mRNA lifetime without negatively influencing other aspects of its functioning is equal to winning a jackpot and is unpredictable, without the benefit of the present application.

Relying on his experience in the development of preparations for gene therapy, the inventor has produced pharmaceutical compositions based on the developed modified gene constructs and pharmaceutically acceptable adjuvants presented by at least one cryoprotectant with filler properties, and a pH stabilizer, which in effective amounts enable preparation of an isotonic solution of plasmid DNA for injections.

A pharmaceutical composition may have the following formulation enabling to preserve properties of the modified plasmid DNA:
    plasmid DNA: from 0.1 to 10 mg/ml, preferably from 0.5 to 4 mg/ml, most preferably from 0.8 to 1.2 mg/ml;
    glucose (dextrose): from 200 to 400 mM, preferably from 250 to 350 mM, most preferably from 280 mM to 320 mM;

sodium phosphate (mixture of trisodium, disodium and monosodium phosphates) at a concentration of 3 to 30 mM, preferably from 5 to 20 mM, most preferably from 8 to 12 mM;

solution pH: from 7.0 to 9.0, preferably from 7.2 to 8.5, most preferably from 7.4 to 8.2.

In one embodiment, the pharmaceutical composition has the following formulation:
plasmid DNA comprising or consisting of the nucleotide sequence of SEQ ID NO:11: 1.2 mg;
dextrose monohydrate: 60 mg;
sodium hydrogen phosphate dodecahydrate: 3.94 mg;
sodium dihydrogen phosphate dehydrate: 0.16 mg.

The composition according to this embodiment was used, as an exemplary composition, in the studies described below in the examples.

The developed gene constructs and pharmaceutical compositions based thereon were studied in vivo on experimental models reproducing the main pathological and pathomorphological symptoms indicative of the diseases known to be suitable for the application of plasmid DNA with the VEGF gene.

The inventor has found that the 3'-UTR of the native VEGF gene (see SEQ ID NO: 1) can be modified or engineered to produce VEGF constructs that reliably and continuously express a VEGF protein when transformed into a host cell. Many examples of such modified or engineered sequences are disclosed herein. These sequences fall within a genus of modified or engineered 3'UTR polynucleotide sequences that are at least 80%, 90%, 95%, or 99% identical to a native 3'-UTR sequence of a VEFG gene, such as that of the 3'-UTR described by SEQ ID NO:1. Such sequences may also be described as sequences which have 1, 2, 3, 4, 5, 6, 7, 8, 9, 10 or more deletions, insertions or substitutions to a native VEFG 3'-UTR sequence.

BLASTN may be used to identify a polynucleotide sequence having at least 70%, 75%, 80%, 85%, 87.5%, 90%, 92.5%, 95%, 97.5%, 98%, 99% sequence identity to a reference polynucleotide. A representative BLASTN setting optimized to find highly similar sequences uses an Expect Threshold of 10 and a Wordsize of 28, max matches in the query range of 0, match/mismatch scores of 1/-2, and linear gap cost. Low complexity regions may be filtered/masked. Default settings are described by and incorporated by reference to the Hypertext Transfer Protocol://blast.ncbi.nlm.nih.gov/
Blast.cgi?PROGRAM=blastn&BLAST_
PROGRAMS=megaBlast&PAGE_TYPE=Blast
Search&SHOWDEFAULTS=on&LINKLOC=blasthome.

BLASTP can be used to identify an amino acid sequence having at least 70%, 75%, 80%, 85%, 87.5%, 90%, 92.5%, 95%, 97.5%, 98%, 99% sequence identity or similarity to a reference amino acid such as a VEGF amino acid sequence using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to the Hypertext Transfer Protocol://blast.ncbi.nlm.nih.gov/
Blast.cgi?PROGRAM=blastp&PAGE_TYPE=
BlastSearch&LINK_LOC=blasthome. Both native and modified or engineered VEFG amino acid (and polynucleotide) sequences are contemplated. A modified or engineered VEGF may exhibit 70, 80, 90, 95, 99% sequence identity to a native VEGF amino acid sequence, such as that encoded by SEQ ID NO: 1 or 11 and/or may exhibit at least one activity of a native VEGF. However, such activity may be enhanced or diminished in relation to a native VEGF, for example, by at least 1, 2, 3, 4, 5, 10, 15, 20, 25, 30, 40, 50, 60, 70, 80, 90, 100, 200, or 400% more or less than a corresponding native VEGF.

Some representative and non-limiting embodiments of the invention include the embodiments described herein.

An engineered polynucleotide that is at least 70, 80, 90, 95, or 99% identical to the VEGF 3'-UTR described in the polynucleotide described by SEQ ID NO:1 [representative native 3'-UTR from a VEGF gene], wherein said engineered polynucleotide contains one or more deletions, substitutions or insertions compared to the VEGF 3'-UTR described in the polynucleotide of SEQ ID NO:1; and wherein said engineered polynucleotide, when present as the 3'-UTR of mRNA encoding vascular endothelial growth factor ("VEGF"), increases the life-time of mRNA encoding VEGF compared to mRNA encoding VEGF having the 3'-UTR sequence of SEQ ID NO:1; or wherein said engineered polynucleotide, when present as the 3'-UTR of mRNA encoding VEGF and expressed in HEK293 cells, increases the expression of VEGF compared to the expression of an otherwise identical mRNA comprising the 3'-UTR sequence of SEQ ID NO:1. The 3'-UTR of the engineered polynucleotide may constitute an untranslated region of a gene selected from the group consisting of VEGF-121, VEGF-145, VEGF-148, VEGF-165, VEGF-183, VEGF-189, and VEGF-206. The 3'-UTR may comprise an untranslated region that contains at least one mutation selected from the group consisting of 1017ΔC, 1079ΔC, 1011ΔT, A1144C, 1048ΔA, 1155ΔC; 1173ΔA, 1083ΔG, 1185ΔC, and G1536C; wherein said nucleotide positions correspond to those given by SEQ ID NO:1.

This engineered polynucleotide may constitute a part of a vector or other DNA construct. Such vectors and constructs may be produced using methods well known in the molecular biological arts and those of skill in these arts may select a suitable vector or construct. Such a vector may further comprise a polynucleotide encoding a polypeptide having at least 70%, 80%, 90%, 95%, or 99% identity to VEGF (encoded by SEQ ID NO:1 or a fragment thereof). The vector according to the invention may comprise at least one mutation selected from the group consisting of 1017ΔC, 1079ΔC, 1011ΔT, A1144C, 1048ΔA, 1155ΔC; 1173ΔA, 1083ΔG, 1185ΔC, and G1536C; wherein said nucleotide positions correspond to those given by SEQ ID NO:1. Combinations of these modifications may also be introduced, such as inclusion of 2, 3, 4, 5, 6, 7, 8, 9 or 10 of the above-described modifications. One example of a vector comprising such a modification is one that contains the polynucleotide sequence of SEQ ID NO:11.

A pharmaceutical composition suitable for regeneration of connective, muscular, neural tissues may be formulated to include the above-described vector. Such a composition may optionally contain at least one cryoprotectant and pH stabilizer or another suitable carrier or excipient.

Another aspect of the invention involves a host cell or other cell that has been transformed or transfected with a vector or DNA construct comprising the engineered 3'-UTR of a VEGF gene that provides for prolonged, reliable and effective expression of VEGF in vitro, ex vivo or in vivo. Such a cell is preferably a living cell that continuously expresses VEFG or can be induced to express VEGF, such as an HEK293 cell. Such a cell may comprise the vector described above and/or at least one other DNA construct. Such cells may be suspended or admixed with at least one pharmaceutically acceptable carrier or excipient and/or with a medium that maintains their viability or modulates their growth or adaptation in vitro, ex vivo or in vivo environments.

Another aspect of the present invention constitutes a method for making a VEGF polypeptide comprising culturing a host cells, such as described above, and recovering a VEGF polypeptide. A VEGF polypeptide according to the present invention may correspond to a full-length native VEGF polypeptide or to a fragment or variant of such a peptide having VEGF activity.

Another aspect of the invention involves a method for regenerating a tissue comprising transforming cells in said tissue with a vector or other polynucleotide construct comprising an engineered 3'-UTR according to the present invention. Representative tissues that may be regenerated include connective, neural, muscular, osseous tissues or cardiovascular system tissue or other organs, tissues or cells that benefit from exposure to VEGF.

Other aspects of the present invention involve a method for engineering a transgene that, when transformed into a HEK293 host cell or other suitable host cell, expresses mRNA encoding VEGF that has an extended lifetime compared to native mRNA encoding VEGF or to mRNA transcribed from the construct described by SEQ ID NO:1. Such a method may comprise one or more of the following steps (i) performing pointwise deletions in a 3'-untranslated region of a vascular endothelial growth factor (VEGF) gene, wherein the deleted nucleotide is either not substituted or substituted with cytosine at the substitution points of guanine and adenine, (ii) determining mRNA lifetime after each deletion, (iii) analyzing the information, and/or (iv) forming a gene construct comprising the 3'-untranslated region with a combination of single deletions and/or substitutions with cytosine having shown the best effect in terms of extension of the mRNA lifetime. Such a method may further comprise transforming a host cell with the engineered transgene and selecting a transformed host cell that expresses a higher amount of VEGF than a host cell expressing native VEGF mRNA or to the VEGF construct described by SEQ ID NO:1. This method may employ a 3'-untranslated region from a gene selected from VEGF-121, VEGF-145, VEGF-148, VEGF-165, VEGF-183, VEGF-189, and VEGF-206 or other isoforms of the vascular endothelial growth factor gene.

All ranges described in this application include all values and subvalues therebetween and the endpoints of each range.

Having generally described this invention, a further understanding can be obtained by reference to certain specific examples which are provided herein for purposes of illustration only, and are not intended to be limiting unless otherwise specified.

EXAMPLE 1

Model of Chronic Ischemia of Lower Limbs

This study was performed using immunodeficient mice (n=90) with the right femoral artery having been cut across in the inguinal region for modeling chronic ischemia of lower limbs (CILL). Two modes were used to administer the pharmaceutical composition based on plasmid DNA according to SEQ ID NO:11: 100 μg once on day 14, and 200 μg twice on days 1 and 14 to the proximal and distal portions of the post-surgical wound. As a control, three groups of animals were used: healthy animals; animals after surgery receiving no substances; and animals after surgery receiving water for injection. The animals were withdrawn from the experiment on 7, 21, or 35 days after surgery, the limbs were subjected to a histological study to determine the number of vessels and a ratio of endotheliocytes to muscle fibers. On days 1, 7, 14, 21, 28, and 35, scanning laser dopplerometry was performed to determine a blood flow perfusion rate in the ischemic and healthy limbs.

Figure 5:
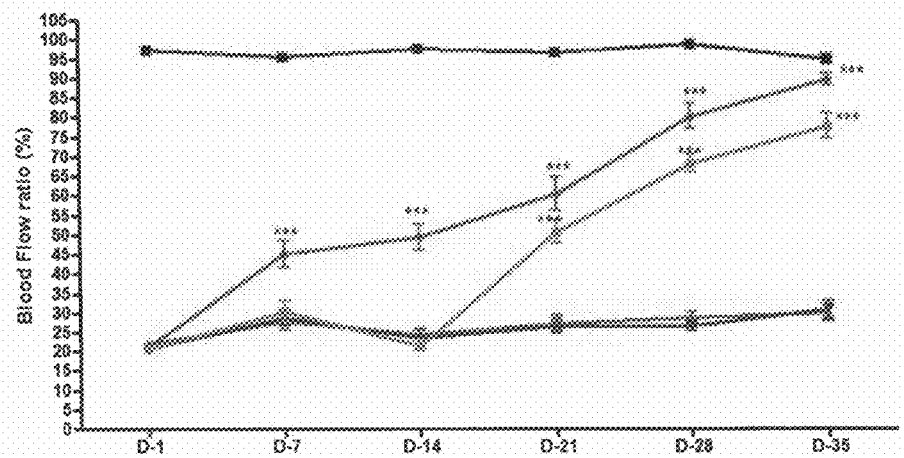
FIG. 5 shows a change in the blood flow perfusion rate in an ischemic limb at different observation times over a 35 day period as described in Example 1. Top trace (healthy animals-no surgery), $2^{nd}$ trace (plasmid comprising SEQ ID NO: 11, 200 mkg once on day 1 and once on day 14); $3^{rd}$ trace (plasmid comprising SEQ ID NO: 11, 100 mkg once on day 14); $4^{th}$ and $5^{th}$ (bottom) traces (after surgery controls: non-treated, water for injection).

Regardless of the dose and mode of administration, the blood flow perfusion rate in the ischemic limb was higher only in the experimental groups 7 days after the administration of the developed preparation for gene therapy. The blood flow perfusion rate was growing and by the end of observations it reached the values close to the parameter of healthy animals. In the control groups of animals after surgery, the blood flow perfusion rate remained at a low level with no positive dynamics (FIG. 5).

Figure 6:
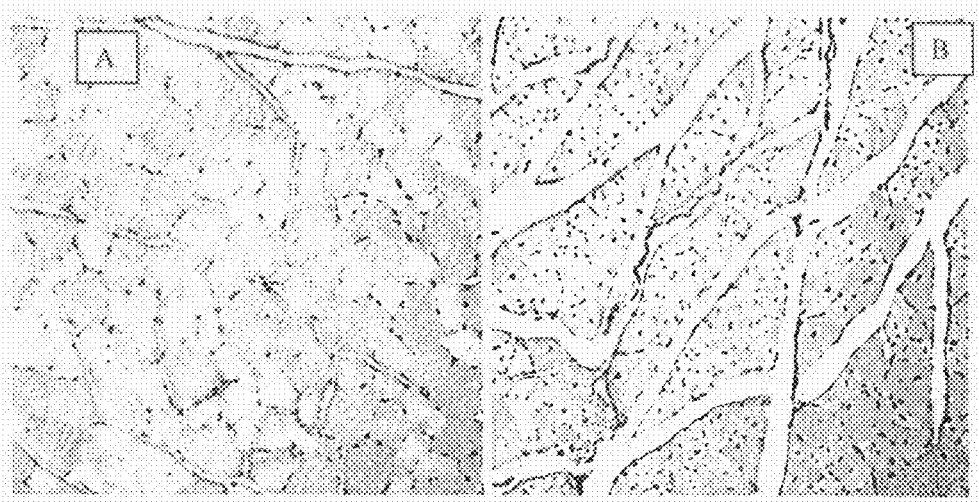
FIG. 6 depicts the state of muscle by histology 35 days after surgery for control animals administered water (FIG. 6A) and animals given 200 mkg of the plasmid comprising SEQ ID NO: 11 on days 1 and 14 (FIG. 6B). Note the difference in vessels between the two samples.
Figure 7:
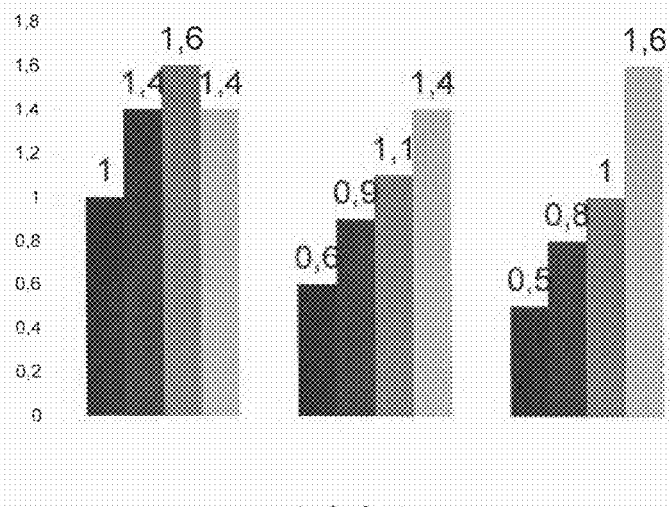
FIG. 7 shows the ratio of $CD34^+$-cells/muscle fibers. Bar 1 (each set)—healthy animals—no surgery; Bar 2 (each set)—after surgery control—non treated; Bar 3 (each set) after surgery control—water for injection; Bar 4 in each set—after surgery administration of SEQ ID NO: 11 plasmid 100 mkg once on day 14.

The functional results were confirmed by histological study findings. More vessels in the experimental groups (FIG. 6) and also a higher ratio of $CD34^+$-cells (endotheliocytes) to the muscle fiber (FIG. 7) have been identified.

EXAMPLE 2

Model of a Critical-sized Bone Defect

The developed gene construct according to SEQ ID NO:11 was combined with a calcium phosphate matrix according to the predetermined protocol.

1. Preparation of a carrier:
   a) ablution (incubation in a 0.5 M phosphate buffer in 1 ml at 37° C. with continuous shaking for 12 hours);
   b) equilibration (treatment with a 10 mM phosphate buffer in 1 ml at 37° C. with continuous shaking, 3 times for 10 min);
   c) drying (incubation at 37° C. until complete drying for 3 hours).

2. Application of a nucleic acid (incubation with solution of plasmid DNA according to SEQ ID NO:11 in a 10 mM phosphate buffer at a concentration of 1 μg/μl at 37° C. with continuous shaking for 12 hours).

3. Treatment of the resulting "carrier-gene construct" complex:
   a) ablution (treatment with a 5 mM phosphate solution in 1 ml 3 times);
   b) drying (incubation at 37° C. until complete drying for 3 hours).

The resulting gene-activated bone graft was studied at orthotropic conditions. The study was performed on Chinchilla rabbits (n=15). In each animal, two identical symmetrical full-thickness defects of both parietal bones with a diameter of 10 mm each were performed, which are "critical" to the rabbits because the natural recovery process never ends in a complete consolidation without optimizing influences. A gene-activated osteoplastic material (experimental group) comprising calcium phosphate and plasmid DNA according to SEQ ID NO:11 was implanted in the defects of right parietal bones, and a carrier without plasmid DNA (control group) was implanted in the defects of left parietal bones. The animals were withdrawn from the experiment on days 30, 60, and 90, and the results were assessed using computer tomography and histological methods.

Due to an originally high density of the selected carrier (about 1800 HU) and the period of its bioresorption (more than 6 months), no objective assessment of evidence of reparative osteogenesis was possible in comparative terms. However, according to the histological study, evidence of osteogenesis was observed in the central part of the defect already 30 days after surgery only where the gene-activated osteoplastic material was used (FIG. 8).

Figure 8:
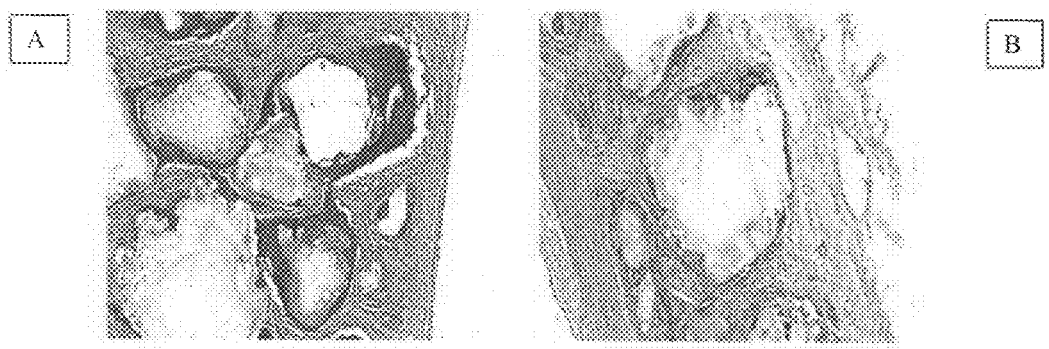
FIG. 8 shows defects in the parietal bones of rabbits 30 days after implantation of osteoplastic materials.
Figure 9:
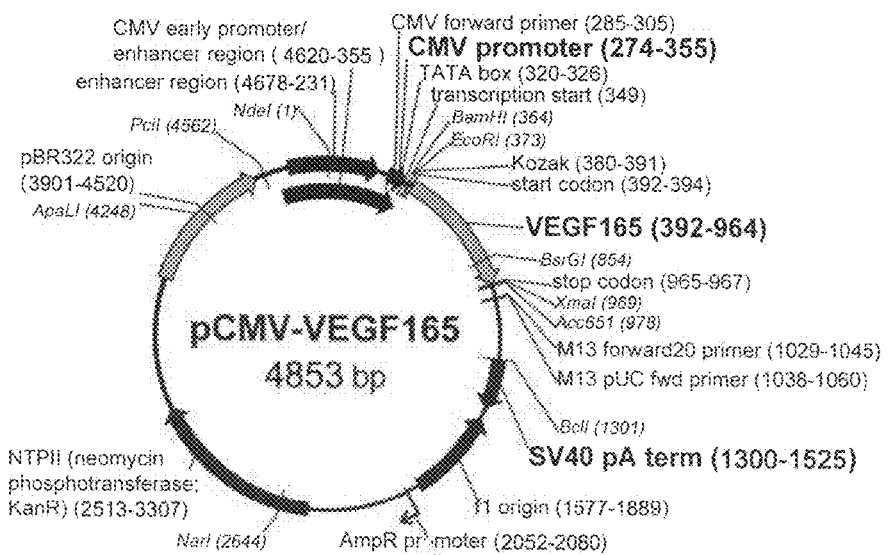
FIG. 9 shows a map of engineered sequence SEQ ID NO:11.

As shown in FIG. 8, material granules in the central part of the defect in the form of loose fibrous connective tissue were the source of reparative osteogenesis whereas in the control defect, calcium phosphate without plasmid DNA was surrounded only by loose fibrous connective tissue without any evidence of the osseous tissue formation. The obtained data is indicative of that plasmid DNA having the nucleotide sequence of SEQ ID NO:11 administered to the area of a critical-sized bone defect resulted in the marked induction of reparative osteogenesis, which may be associated both with the angiogenesis-mediated effect and direct influence of VEGF on a mesenchymal cell line.

Therefore, the above examples illustrate that the developed modified gene construct and a pharmaceutical composition based thereon have a marked angiogenic activity so that it can be used for treatment of ischemic diseases of the cardiovascular system. In addition, the modified gene construct with the VEGF gene may be efficient for treatment of other pathological conditions that require activation of a reparative process, such as injuries of skin and locomotor apparatus, injuries of peripheral nerves, diabetic foot syndrome, and amyotrophic lateral sclerosis.

Numerous modification and variations on the present invention are possible in light of the above teachings. It is therefore to be understood that within the scope of the appended claims, the invention may be practiced otherwise than as specifically described herein.

All publications, patent applications, patents, and other references mentioned herein are incorporated by reference in their entirety. Further, the materials, methods, and examples are illustrative only and are not intended to be limiting, unless otherwise specified.

As used herein the words "a", "an" and the like generally carry a meaning of "one or more", unless stated otherwise. The drawings are generally drawn to scale unless specified otherwise or illustrating schematic structures or flowcharts.

Literature:

1. Gene therapy clinical trials worldwide. Hypertext Transfer Protocol://www.abedia.com/wiley/years.php.

2. Grigorian A. S., Schevchenko K. G. Some possible molecular mechanisms of VEGF coding plasmids functioning. Cell. Tanspl. Tiss. Engin. 2011. VI (3): 24-8.

3. Baboo S., Cook P. R. "Dark matter" worlds of unstable RNA and protein. Nucleus 2014; 5(4): 281-6.

4. Vislovukh A., Vargas T. R., Polesskaya A. et al. Role of 3'-untranslated region translational control in cancer development, diagnostics and treatment. World J. Biol. Chem. 2014; 5(1): 40-57.

5. Malter J. Method to increase regulatory molecule production. U.S. Pat. No. 5,587,300; Dec. 24, 1996.

6. Sytkowski A. J., Grodberg J. Erythropoietin DNA having modified 5' and 3' sequences and its use to prepare EPO therapeutics. U.S. Pat. No. 6,153,407; Nov. 28, 2000

7. Mauro V. P., Chappell S. A., Zhou W. et al. Reengineering mRNA primary construct for enhanced protein production. US patent application No. 2012/0,053,333 A1; Mar. 1, 2012.

8. Folkman J., Merler E., Abernathy C. et al. Isolation of a tumor factor responsible for angiogenesis. J. Exp. Med. 1971; 133(2): 275-88.

9. Goel H. L., Mercurio A. M. VEGF targets the tumour cell. Nat. Rev. Cancer. 2013; 13(12): 871-82.

10. Koch S., Claesson-Welsh L. Signal transduction by vascular endothelial growth factor receptors. Cold Spring Harb. Perspect. Med. 2012; 2(7): a006502.

11. Matsumoto T., Bohman S., Dixelius J. et al. VEGF receptor-2 Y951 signaling and a role for the adapter molecule TSAd in tumor angiogenesis. EMBO J. 2005; 24(13): 2342-53.

12. Bhattacharya R., Kwon J., Li X. et al. Distinct role of PLCbeta3 in VEGF-mediated directional migration and vascular sprouting. J. Cell Sci. 2009; 122(Pt 7): 1025-34.

13. Coultas L., Chawengsaksophak K., Rossant J. Endothelial cells and VEGF in vascular development. Nature 2005; 438(7070): 937-45.

14. Olsson A. K., Dimberg A., Kreuger J. et al. VEGF receptor signalling—in control of vascular function. Nat. Rev. Mol. Cell Biol. 2006; 7(5): 359-71.

15. Ma X. N., Li Q. P., Feng Z. C. Research progress in cytokines and signaling pathways for promoting pulmonary angiogenesis and vascular development. Zhongguo Dang Dai Er Ke Za Zhi. 2013; 15(9): 800-5.

16. Arutyunian I. V., Kananykhina E. Yu., Makarov A. V. Role of VEGF-A165 receptors in angiogenesis. Cellular Transplantology and Tissue, 2013; VIII(1): 12-8.

17. Cherviakov Yu. A., Staroverov I. N., Nersesian E. G. et al. The opportunities for genic therapy of chronic obliterating diseases of lower limbs arteries. Khirurgiia (Mosk). 2014; (4): 40-5.

18. Willyard C. Limb-saving medicines sought to prevent amputation. Nature Medicine 2012; 18(3): 328.

19. Hillenbrand M., Holzbach T., Matiasek K. et al. Vascular endothelial growth factor gene therapy improves nerve regeneration in a model of obstetric brachial plexus palsy. Neurol Res. 2015; 37(3): 197-203.

20. Kessler J A. Vascular endothelial growth factor gene transfer for diabetic polyneuropathy. Ann Neurol. 2009; 65(4): 362-4.

21. Zavalishin I. A., Bochkov N. P., Suslina Z. A. et al. Gene therapy of amyotrophic lateral sclerosis. Bull Exp Biol Med. 2008; 145(4): 483-6.

22. Zhao D. M., Yang J. F., Wu S. Q. et al. Effect of vascular endothelial growth factor 165 gene transfection on repair of bone defect: experiment with rabbits. Zhonghua Yi Xue Za Zhi. 2007; 87(25): 1778-82.

23. Geiger F., Bertram H., Berger I. et al. Vascular endothelial growth factor gene-activated matrix (VEGF165-GAM) enhances osteogenesis and angiogenesis in large segmental bone defects. J. Bone Miner. Res. 2005; 20(11): 2028-35.

24. Neve A., Cantatore F. P., Corrado A. et al. In vitro and in vivo angiogenic activity of osteoarthritic and osteoporotic osteoblasts is modulated by VEGF and vitamin D3 treatment. Regul. Pept. 2013; 184: 81-4.

25. Marini M., Sarchielli E., Toce M. et al. Expression and localization of VEGF receptors in human fetal skeletal tissues. Histol. Histopathol. 2012; 27(12): 1579-87.

26. Tombran-Tink J., Barnstable C. J. Osteoblasts and osteoclasts express PEDF, VEGF-A isoforms, and VEGF receptors: possible mediators of angiogenesis and matrix remodeling in the bone. Biochem. Biophys. Res. Commun. 2004; 316(2): 573-9.

27. Mayr-Wohlfart U., Waltenberger J., Hausser H. et al. Vascular endothelial growth factor stimulates chemotactic migration of primary human osteoblasts. Bone 2002; 30(3): 472-7.

28. D'Alimonte I., Nargi E., Mastrangelo F. et al. Vascular endothelial growth factor enhances in vitro proliferation and osteogenic differentiation of human dental pulp stem cells. J. Biol. Regul. Homeost. Agents. 2011; 25(1): 57-69.

29. Yang Y. Q., Tan Y. Y., Wong R. et al. The role of vascular endothelial growth factor in ossification. Int. J. Oral Sci. 2012; 4(2): 64-8.

30. Berendsen A. D., Olsen B. R. How vascular endothelial growth factor-A (VEGF) regulates differentiation of mesenchymal stem cells. J. Histochem. Cytochem. 2014; 62(2): 103-8.

The invention claimed is:

1. A method for extending the lifetime of mRNA encoding vascular endothelial growth factor (VEGF) in a host cell comprising:
   performing at least one modification selected from the group consisting of at least one pointwise single deletion of guanine, adenosine, thiamine, or cytosine, and at least one pointwise single substitution of guanine or adenosine with cytosine, in the 3'-untranslated region of a VEGF gene to produce at least one engineered polynucleotide;
   transforming the at least one engineered polynucleotide into a host cell,
   determining lifetime of said at least one mutant mRNA in the host cell, wherein when the engineered polynucleotide is transformed into and transcribed by the host cell, the at least one mutant mRNA is its transcription product, and
   selecting at least one mutant mRNA that has an extended lifetime compared to lifetime of an otherwise identical control mRNA which is a transcription product of the VEGF gene that has not been mutated.

2. The method according to claim 1, wherein the at least one mutant mRNA increases a level of VEGF expressed compared to a level expressed by the control non-mutated mRNA.

3. The method according to claim 1, wherein the VEGF gene encodes an isoform selected from the group consisting of VEGF-121, VEGF-145, VEGF-148, VEGF-165, VEGF-183, VEGF-189, and VEGF-206.

4. The method according to claim 1, wherein the host cell is a mammalian cell.

5. The method according to claim 1, wherein the host cell is obtained from a subject in need of increased expression of VEGF.

6. The method according to claim 1, wherein the VEGF gene that has not been mutated comprises the polynucleotide of SEQ ID NO:1.

7. The method according to claim 1, wherein the at least one modification comprises at least one nucleotide sequence modification selected from the group consisting of
   C-deletion at position 1071,
   C-deletion at position 1079,
   T-deletion at position 1111,
   A/C-substitution at position 1144,
   A-deletion at position 1148,
   C-deletion at position 1155,
   A-deletion at position 1173,
   G-deletion at position 1083,
   A-deletion at position 1185, and
   G/C-substitution at position 1536;
   wherein the positions correspond to those of SEQ ID NO: 1.

8. The method according to claim 1, wherein the engineered polynucleotide comprises a polynucleotide selected from the group consisting of SEQ ID NO:2 to SEQ ID NO:10 and SEQ ID NO:11.

9. The method according to claim 8, wherein the engineered polynucleotide comprises the polynucleotide of SEQ ID NO: 11.

* * * * *